(12) United States Patent  
Krautkramer et al.

(10) Patent No.: US 7,858,841 B2
(45) Date of Patent: Dec. 28, 2010

(54) ENHANCED BODY CONFORMANCE WITH THE USE OF FREE FLOWING PARTICLES

(75) Inventors: Patsy A. Krautkramer, Omro, WI (US); William G. Reeves, Appleton, WI (US); Heather A. Sorebo, Appleton, WI (US); Garry R. Woltman, Greenville, WI (US); Wendy L. Hamilton, Neenah, WI (US); Emmanuelle C. Damay, Erlangen (DE); Bernhardt E. Kressner, Appleton, WI (US); William G. Stoeger, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1184 days.

(21) Appl. No.: 10/316,392

(22) Filed: Dec. 11, 2002

(65) Prior Publication Data

US 2004/0116883 A1 Jun. 17, 2004

(51) Int. Cl.
*A61F 13/15* (2006.01)
(52) U.S. Cl. ...................... 604/367; 604/359
(58) Field of Classification Search ................ 604/367, 604/364, 378, 385.01, 385.101, 383, 368
See application file for complete search history.

(56) References Cited

U.S. PATENT DOCUMENTS

| | | | |
|---|---|---|---|
| 4,055,180 A | 10/1977 | Karami | |
| 4,327,728 A | 5/1982 | Elias | |
| 4,433,972 A | 2/1984 | Malfitano | |
| RE32,957 E | 6/1989 | Elias | |
| 4,846,824 A | 7/1989 | Lassen et al. | |
| 5,509,915 A * | 4/1996 | Hanson et al. | 604/378 |
| 5,762,641 A * | 6/1998 | Bewick-Sonntag et al. | 604/378 |
| 5,891,126 A | 4/1999 | Osborn, III et al. | |
| 5,938,650 A | 8/1999 | Baer et al. | |

(Continued)

FOREIGN PATENT DOCUMENTS

EP 0 483 730 A1 5/1992

(Continued)

OTHER PUBLICATIONS

Webb, Paul A. and Clyde Orr, *Analytical Methods in Fine Particle Technology*, Chapters 3 and 4, Micromeritics Instrument Corp., 1997, pp. 53-191.

(Continued)

*Primary Examiner*—Melanie J Hand
(74) *Attorney, Agent, or Firm*—Paul Yee; Bryan Rosiejka; David Arteman

(57) ABSTRACT

A body conformance system (22) includes at least one liquid-permeable, flexible containment layer (24), and an operative quantity of substantially free-flowing particulate material (28) constrained by the flexible containment layer (24). In a particular aspect, the substantially free-flowing particulate material (28) can exhibit a selected avalanche-time between avalanches. In another aspect, the particulate material can exhibit a selected, minimum retention capacity. In a further aspect, the system can exhibit a distinctive gap-protrusion area (104). In yet another aspect, the containment layer (24) can include a material that has a relatively high permeability to liquid, but a relatively high resistance to a passage of the particulate material.

25 Claims, 20 Drawing Sheets

U.S. PATENT DOCUMENTS

| | | | |
|---|---|---|---|
| 5,977,430 A | 11/1999 | Roe et al. | |
| 6,010,491 A | 1/2000 | Roe et al. | |
| 6,013,063 A | 1/2000 | Roe et al. | |
| 6,409,883 B1 * | 6/2002 | Makolin et al. | 162/52 |
| 6,455,114 B1 | 9/2002 | Goldhirsch et al. | |
| 7,278,988 B2 * | 10/2007 | Molas et al. | 604/385.201 |
| 2002/0102392 A1 | 8/2002 | Fish et al. | |

FOREIGN PATENT DOCUMENTS

| | | |
|---|---|---|
| EP | 0 526 225 A1 | 2/1993 |
| EP | 0 779 065 A2 | 6/1997 |
| EP | 0 875 224 A1 | 11/1998 |
| EP | 0 971 751 B1 | 1/2000 |
| WO | WO 98/36720 A1 | 8/1998 |
| WO | WO 99/25294 A1 | 5/1999 |
| WO | WO 00/62730 A1 | 10/2000 |
| WO | WO 00/62825 A2 | 10/2000 |
| WO | WO 00/62826 A1 | 10/2000 |
| WO | WO 00/62922 A1 | 10/2000 |
| WO | WO 00/63486 A1 | 10/2000 |
| WO | WO 00/63487 A1 | 10/2000 |
| WO | WO 00/63492 A1 | 10/2000 |
| WO | WO 01/06974 A1 | 2/2001 |

OTHER PUBLICATIONS

Neumann, A.W., and R.J. Good, "Techniques of Measuring Contact Angles," Chapter 2 of *Surface and Colloid Science*, vol. 11, Experimental Methods, edited by R.J. Good and R.R. Stromberg, Plenum Press, 1979, pp. 31-91.

Federal Test Method Standard (FTMS) No. 191A, Method 5514, "Water Resistance of Cloth; Low Range, Hydrostatic Pressure Method," Jul. 20, 1978, 3 pages.

* cited by examiner

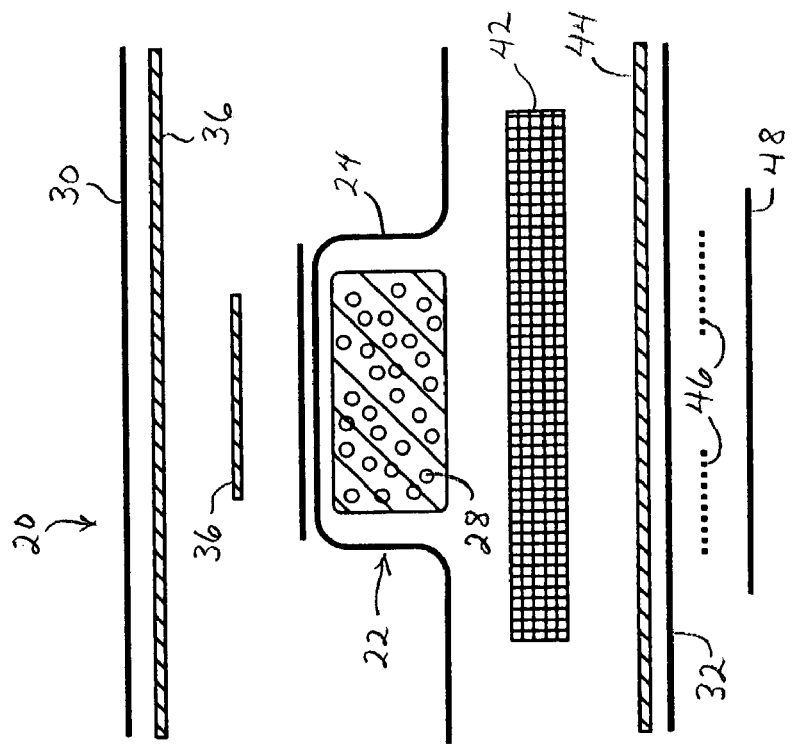
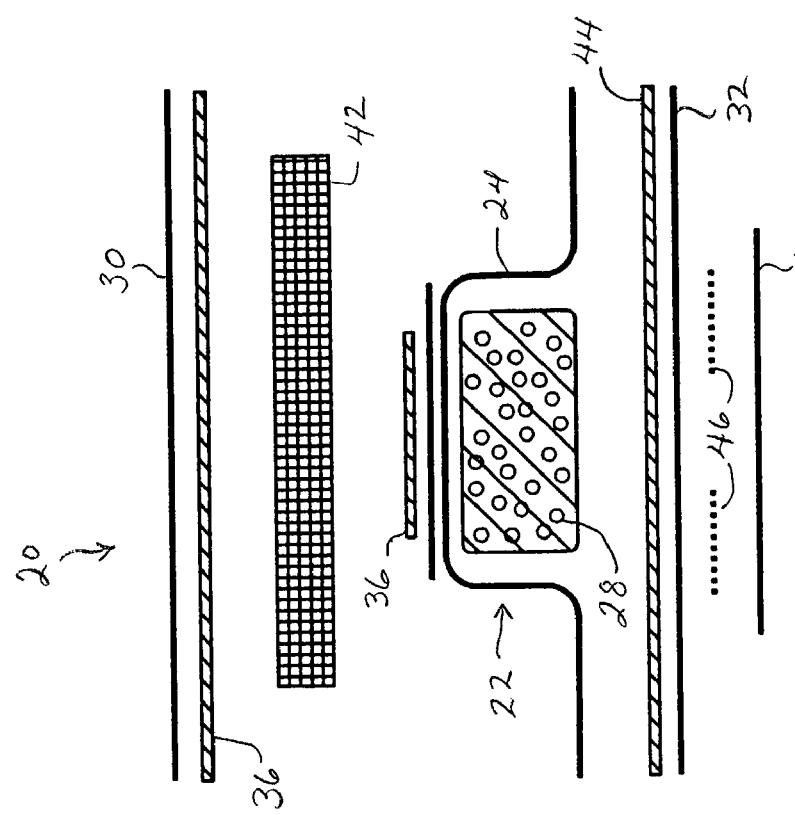

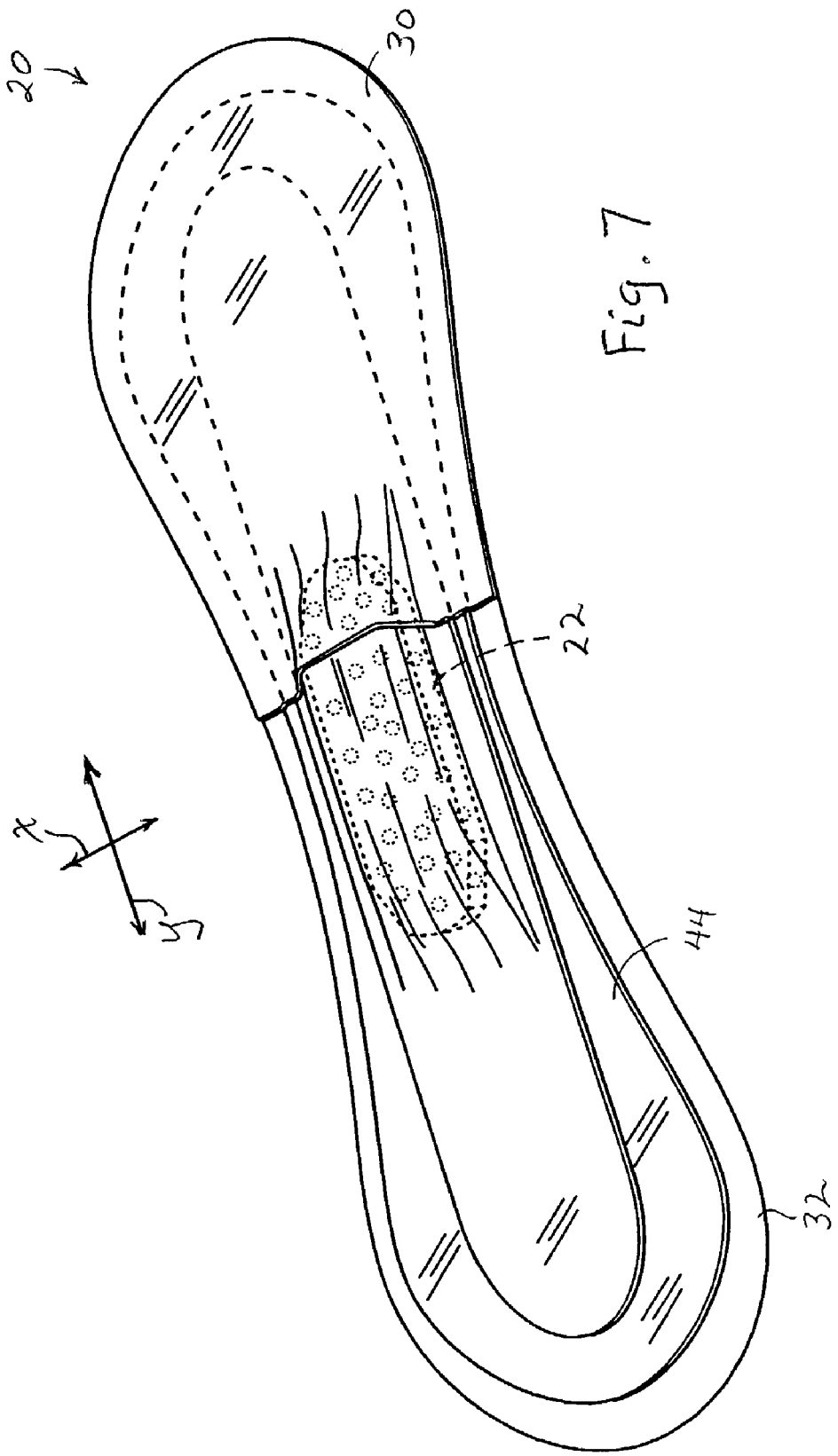

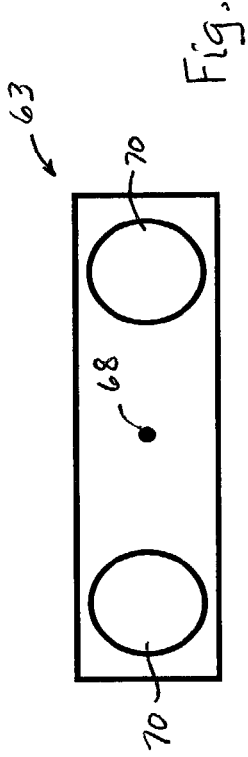
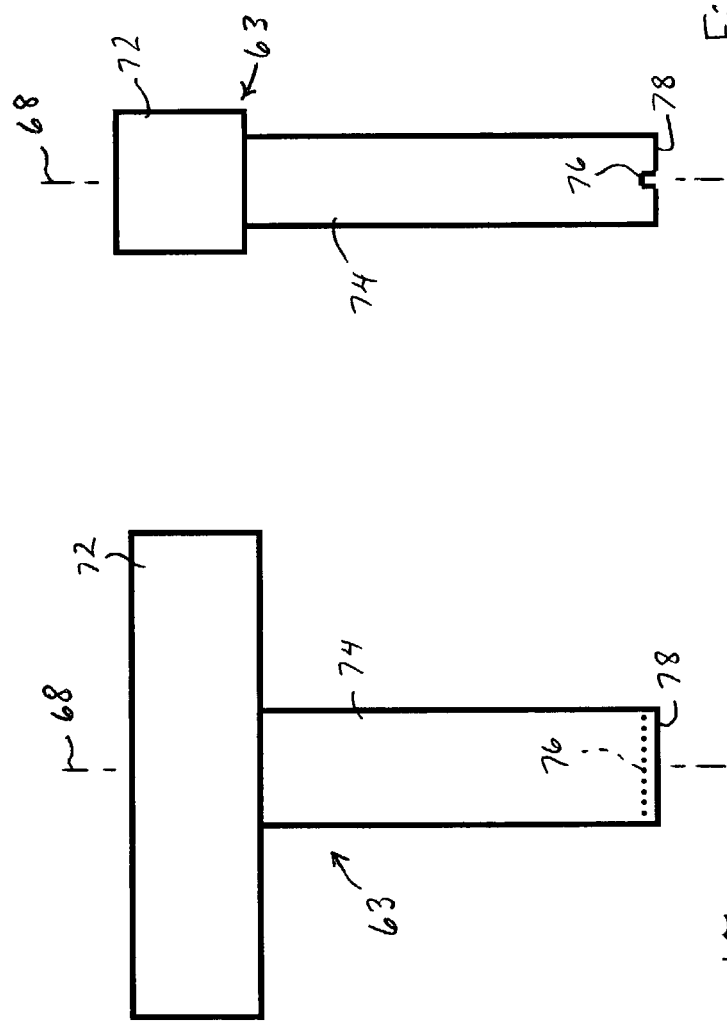

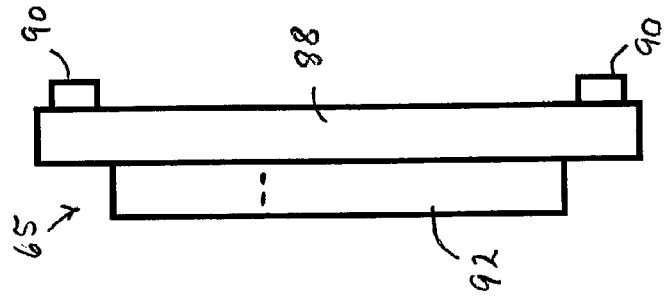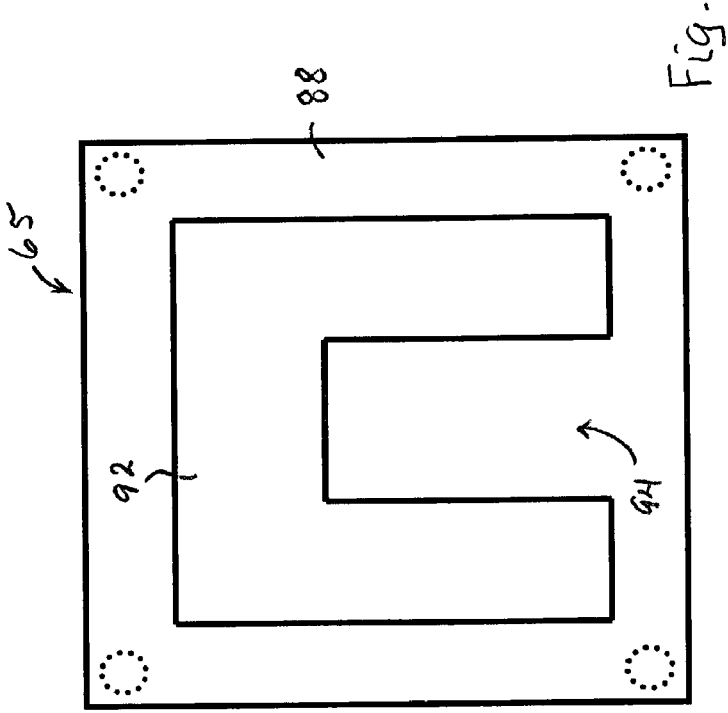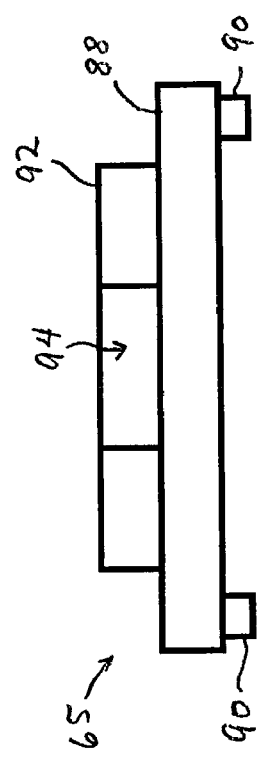

ENHANCED BODY CONFORMANCE WITH THE USE OF FREE FLOWING PARTICLES

BACKGROUND

The present invention relates to a system and article for producing an enhanced body conformance. More particularly, the present invention can provide a system and article which can enhance body conformance with the use of free flowing particles.

The use of adsorbent particles in disposable absorbent articles is known. Such adsorbent particles are generally employed on a somewhat limited basis for odor control in disposable personal care absorbent articles. However, a more widespread use of such adsorbent particles in absorbent structures and disposable absorbent articles has been somewhat confined by the limited efficacy of the adsorbent particles in the handling of complex liquids. As a result, there has been a continued need for improved systems and articles that can more effectively provide desired levels of body conformance, along with rapid uptake and good retention of liquid-complexes, such as complex body-liquids. Such improved systems and articles can potentially enhance the operation of the adsorbent particles in disposable absorbent articles, as well as other absorbent structures.

BRIEF DESCRIPTION OF THE INVENTION

The present inventors have recognized the difficulties and problems that are present in the prior art, and in response thereto, have conducted intensive research into developing adsorbent particles that can more effectively handle and process complex body-liquids. While conducting such research, the inventors found that certain adsorbent materials exhibit an enhanced efficacy in the handling and processing of complex liquids. The efficacy of these adsorbent materials can be improved by an appropriate selection and configuration of the adsorbent materials. As a result of the improved performance, the adsorbent materials of the present invention can allow for a distinctive incorporation and use of adsorbent particles in disposable absorbent articles, disposable personal care articles, and other absorbent structures.

Generally stated, the present invention can provide a body-conformance system which can be positioned at least operatively proximate a bodyside surface of an article. The body conformance system includes at least one liquid-permeable, flexible containment layer, and an operative quantity of substantially free-flowing particulate material constrained by said flexible containment layer. In a particular aspect, the substantially free-flowing particulate material can have a distinctive avalanche-time. Another aspect of the invention can include a configuration that provides a distinctive gap-protrusion area. In a further aspect, the particulate material can have a distinctive retention capacity. Yet another aspect of the invention can include a containment layer which is configured to provide an operative containment of the particulate material and a high rate of liquid flow-through. An additional aspect can include a containment layer which is configured to provide a selected intake-handling time.

In its various aspects and features, the present invention can provide an article and system that can provide an enhanced body conformance in a selected article. In particular, the present invention can provide an article and system that can provide improved body conformance and comfort, while also providing a rapid uptake and good retention of a selected liquid, such as a complex-liquid.

DRAWINGS

The various features, aspects and advantages of the present invention will become better understood with reference to the following description, appended claims and accompanying drawings where:

Figure 3:
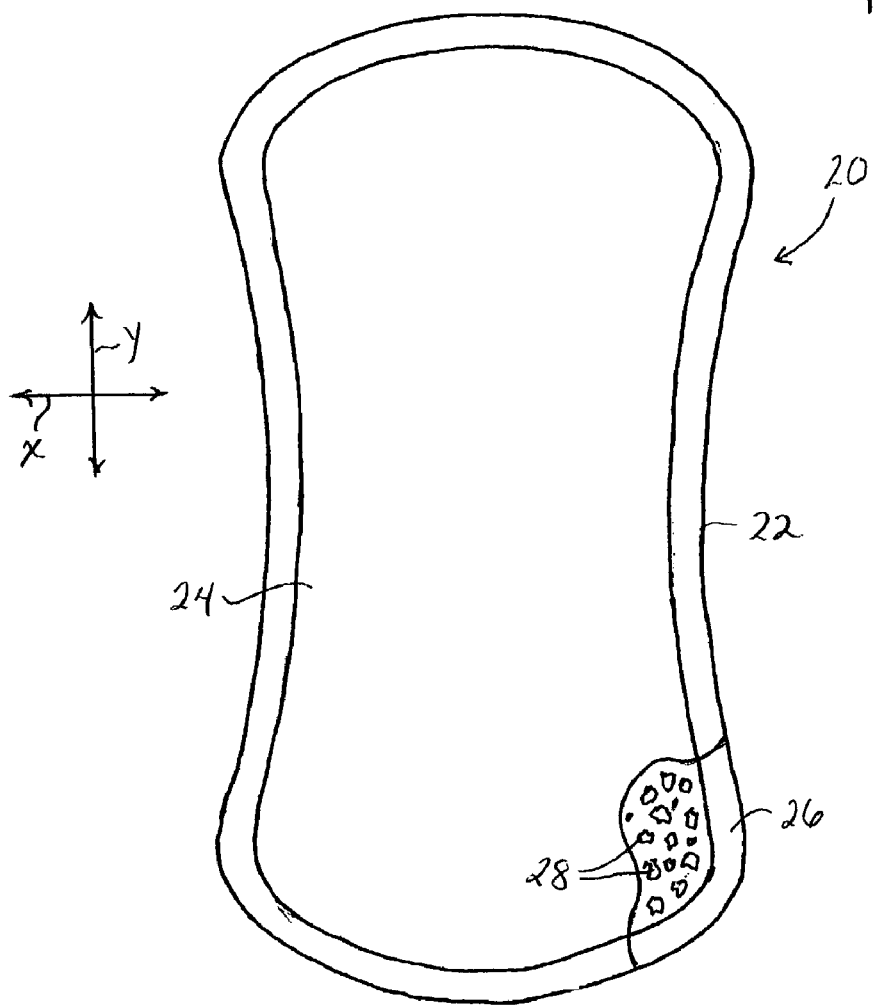

FIG. 3 representatively shows a partially cut-away, top plan view of a pad article which incorporates the system of the invention and has a bodyside layer and a garment-side layer.

Figure 4:
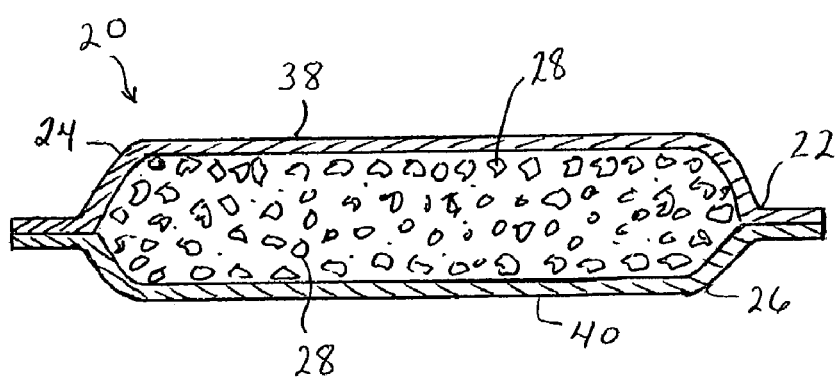

FIG. 4 shows a representative end-wise view of a cross-section through a pad article which incorporates a bodyside layer and a garment-side layer.

FIG. 5 is a schematic end-view of a cross-section through a representative absorbent article having a body-conformance system and an absorbent retention portion.

FIG. 6 is a schematic end-view of a cross-section through a representative absorbent article having another arrangement of a body-conformance system and a retention portion.

FIG. 7 is perspective view of an absorbent article having a body-conformance system and a retention portion.

Figure 8:
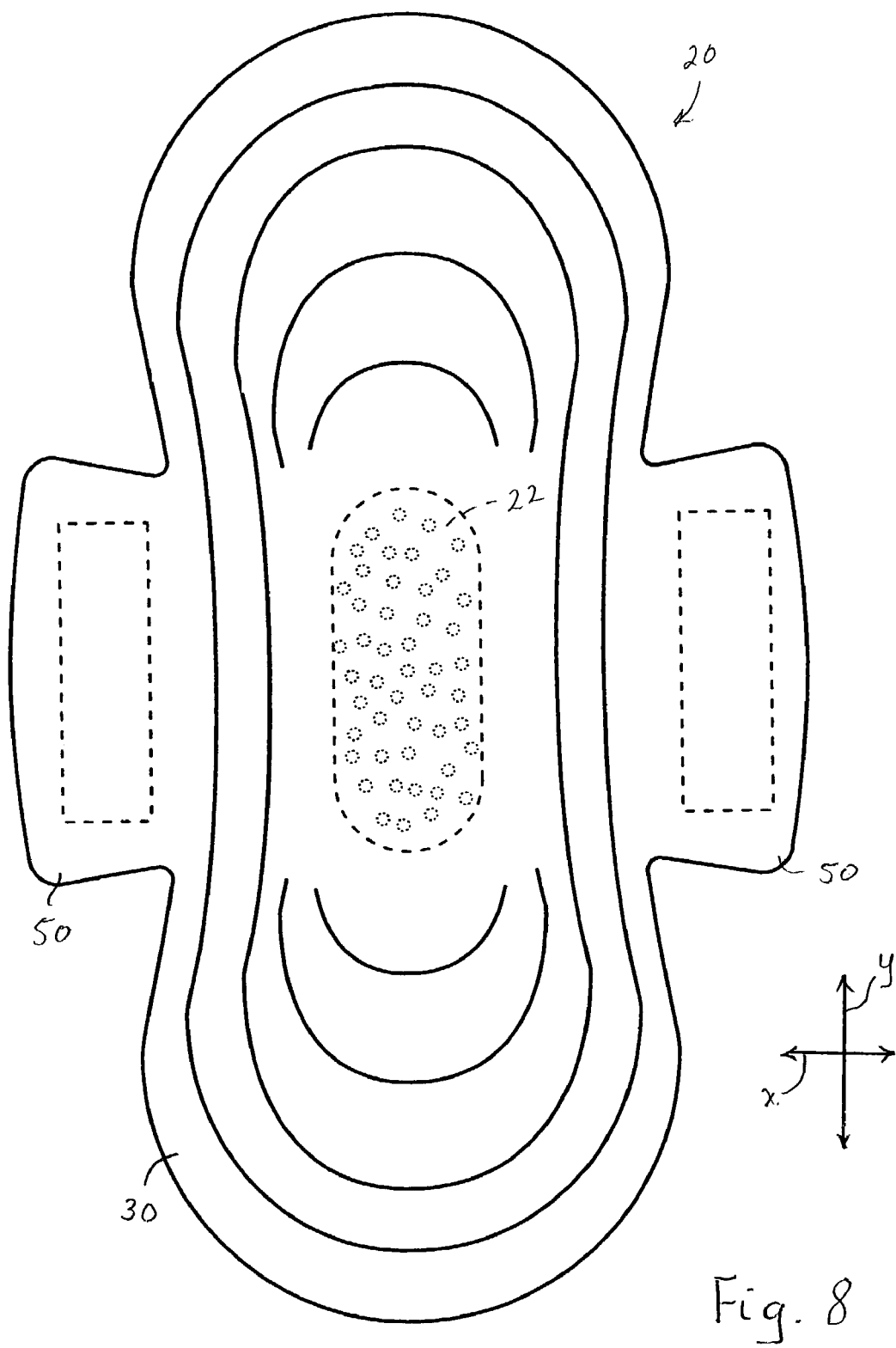

FIG. 8 is a top, plan view of a representative absorbent article having a body-conformance system and wing members for holding the article in an undergarment.

Figure 9:
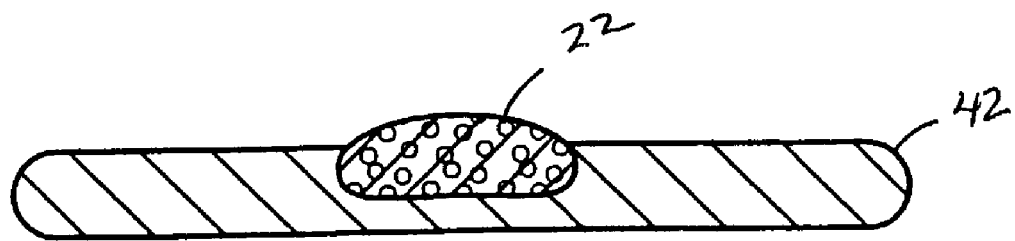

FIG. 9 is a schematic end-view of a cross-section through a representative absorbent article having a body-conformance system which is partially sunken into a thickness of a retention portion.

Figure 9A:
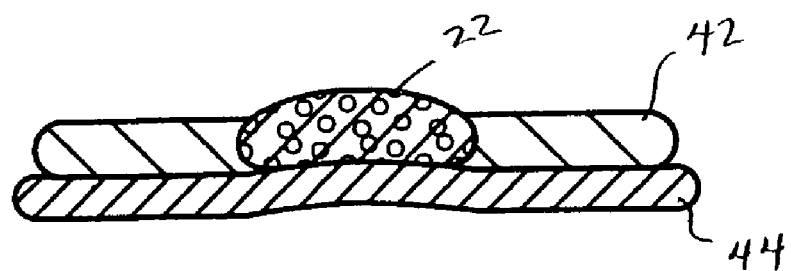

FIG. 9A is a schematic end-view of a cross-section through a representative absorbent article having a body-conformance system which is sunken through a total thickness of a retention portion.

Figure 9B:
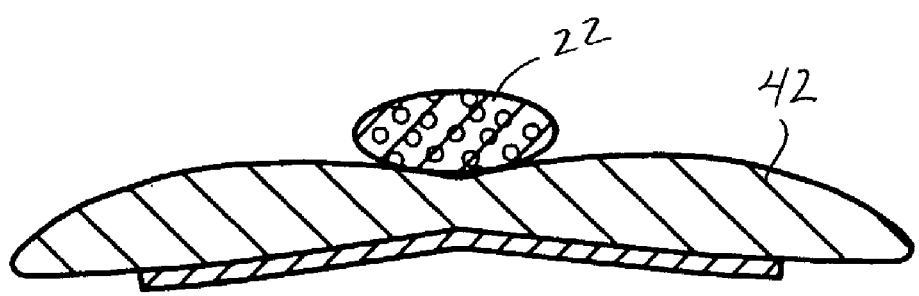

FIG. 9B is a schematic end-view of a cross-section through a representative absorbent article having a body-conformance system which is superposed onto a retention portion.

Figure 10:
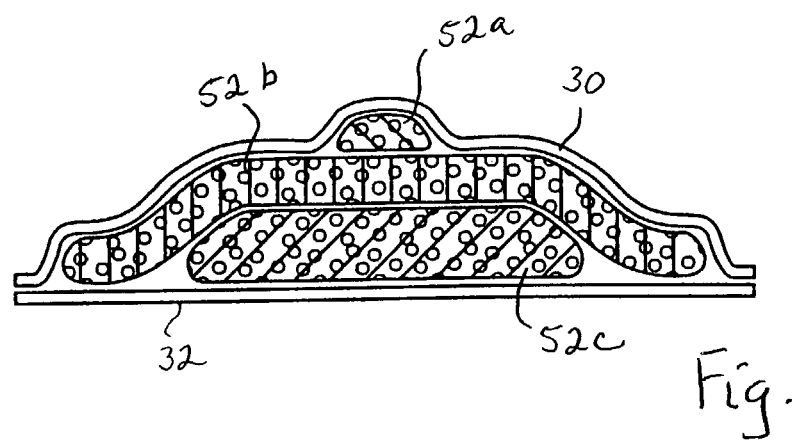

FIG. 10 is a schematic end-view of a cross-section through a representative absorbent article having a body-conformance system which is incorporated into two or more layer regions.

Figure 10A:
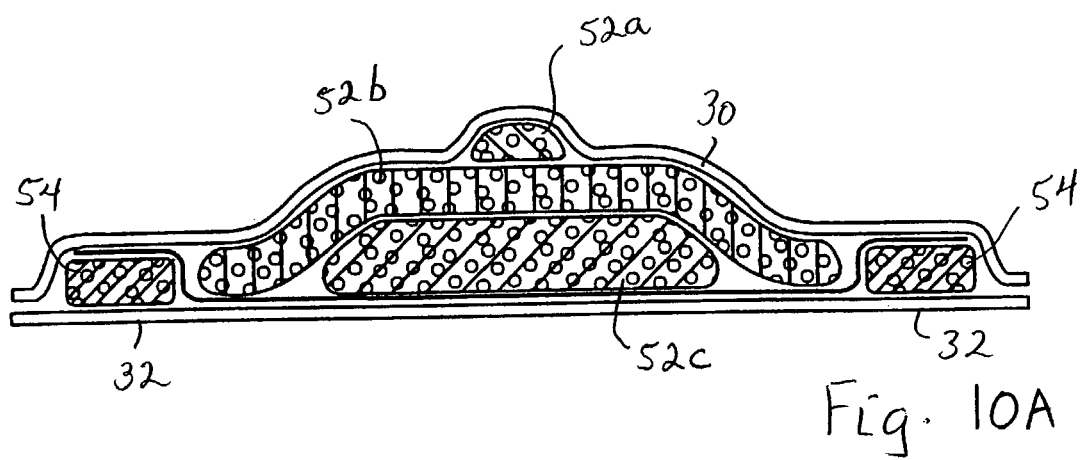

FIG. 10A is a schematic end-view of a cross-section through a representative absorbent article having a body-conformance system which is incorporated into one or more edge layer regions.

Figure 11:
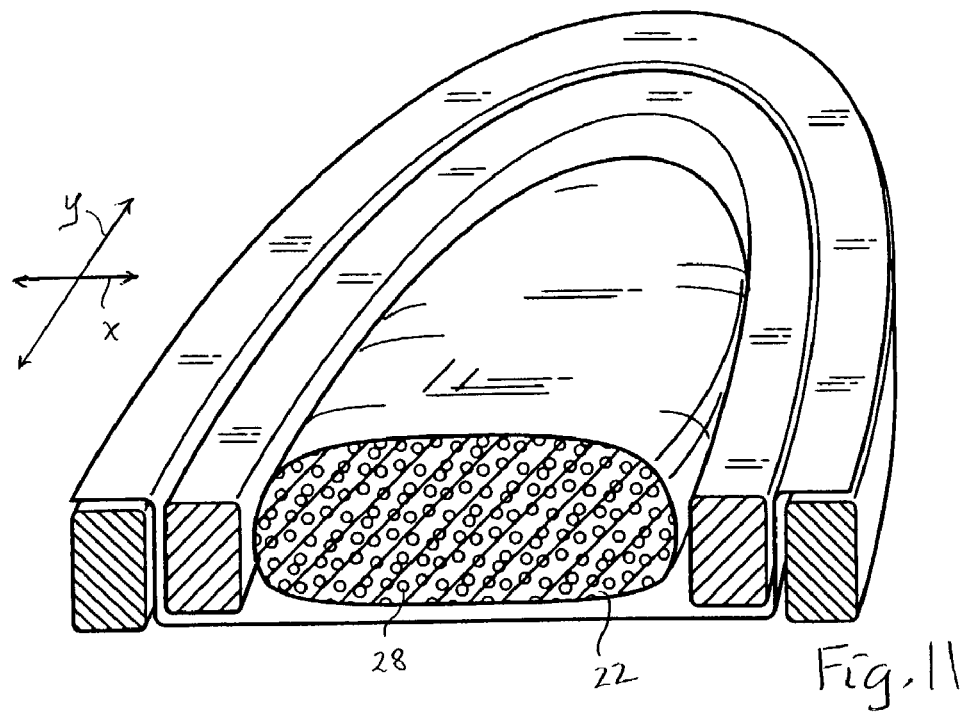

FIG. 11 is a perspective view of a cross-section through a representative article having a body-conformance system arranged in a medial position with respect to an array of absorbent components that are distributed along the x-y, width and length dimensions of the article.

Figure 11A:
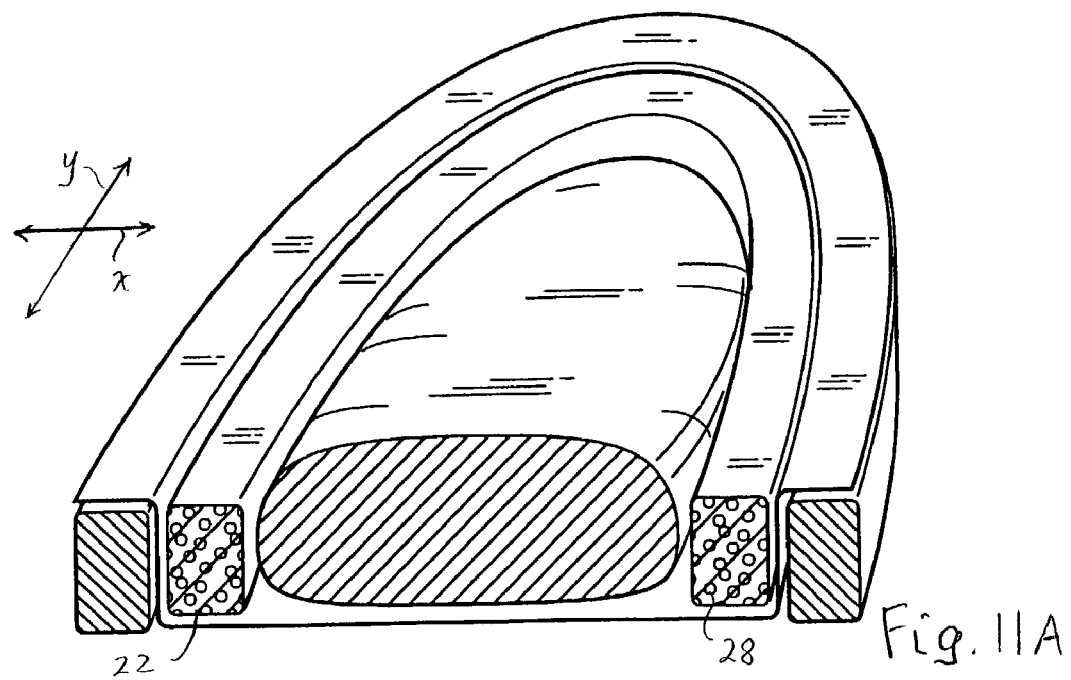

FIG. 11A is a perspective view of a cross-section through another representative article having a body-conformance system arranged in an intermediate position with respect to an array of absorbent components that are distributed along x-y dimensions of the article.

Figure 11B:
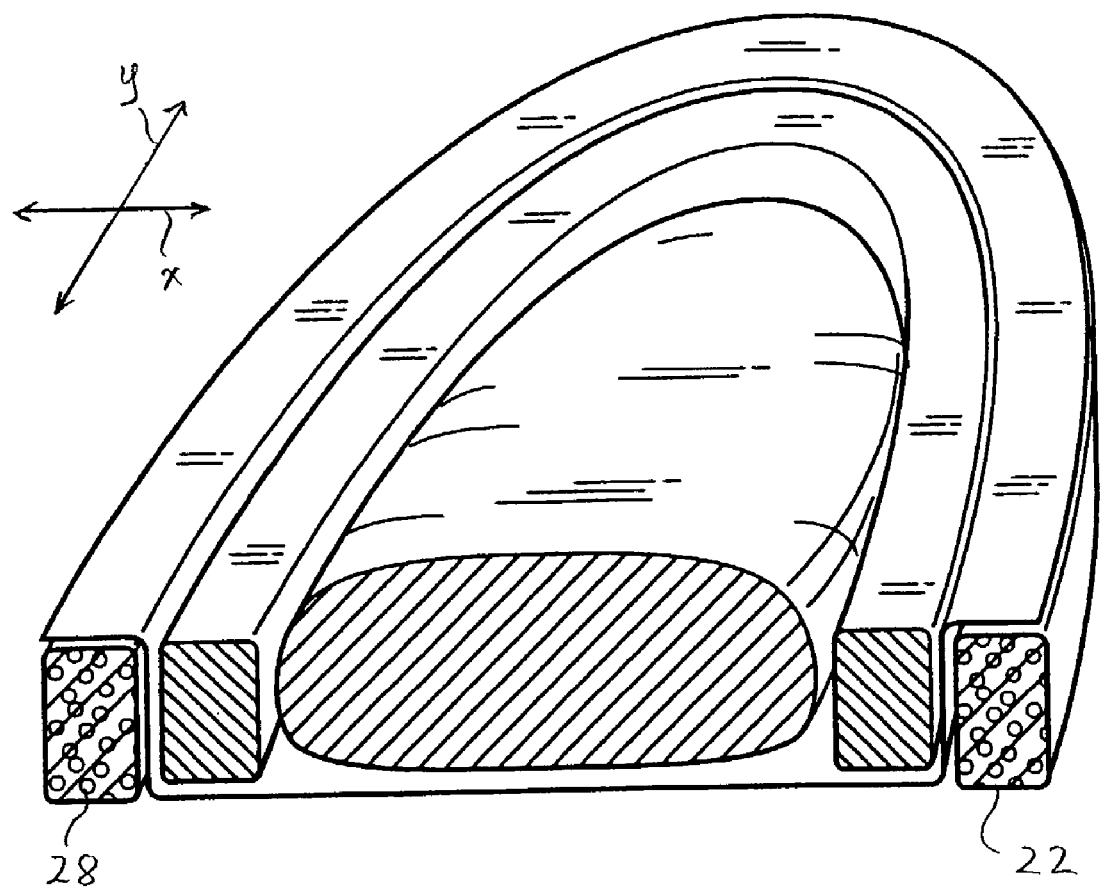

FIG. 11B is a perspective view of a cross-section through still another representative article having a body-conformance system arranged in an outboard position with respect to an array of absorbent components that are distributed along x-y dimensions of the article.

Figure 12:
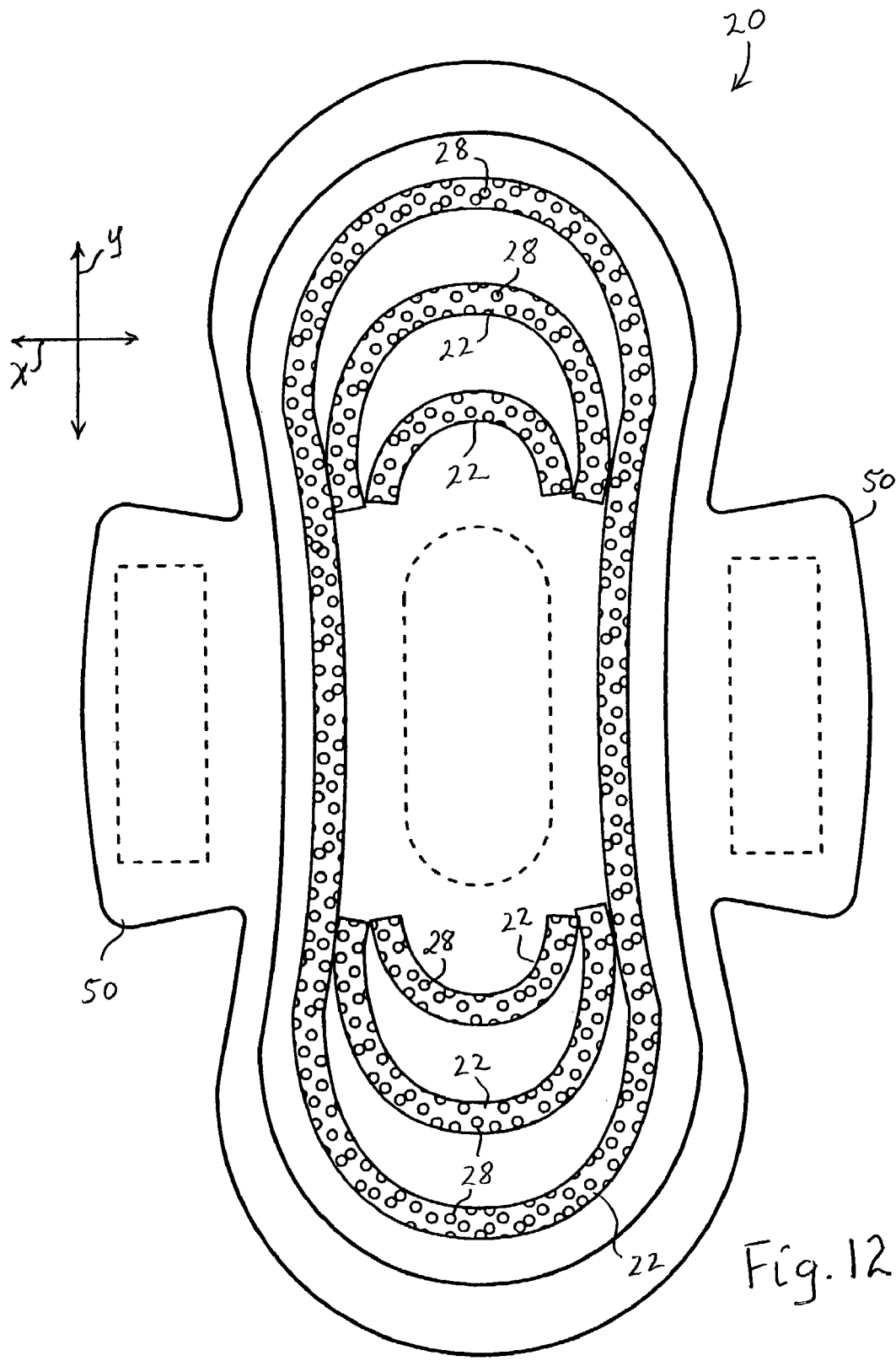

FIG. 12 is a representative top, plan view of an article having a body-conformance system that is configured with an array of individual body-conformance components that are distributed along x-y dimensions of the article.

Figure 13:
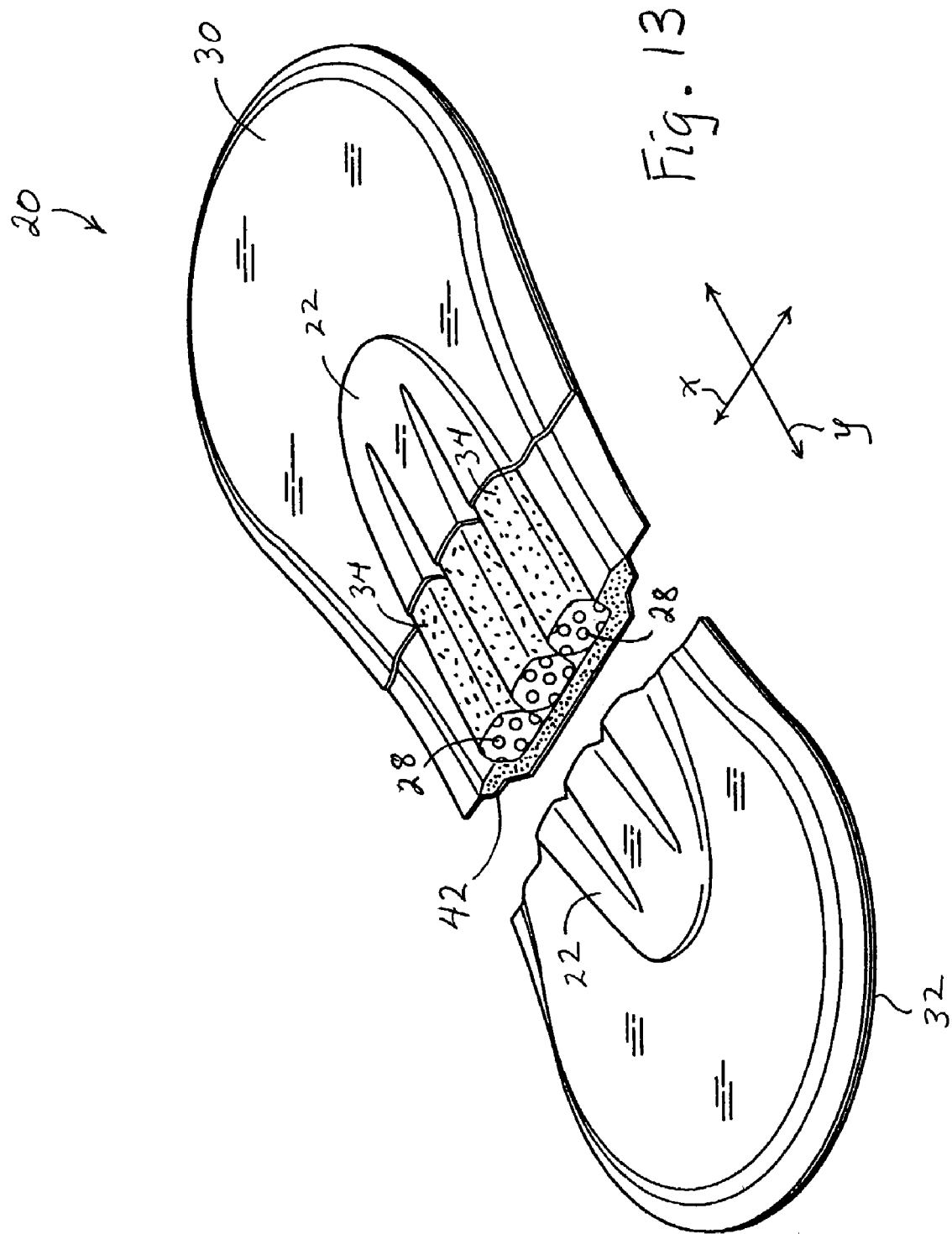

FIG. 13 is a representative, perspective view of a partially sectioned article having a body conformance system configured with a varying, contour.

Figure 14:
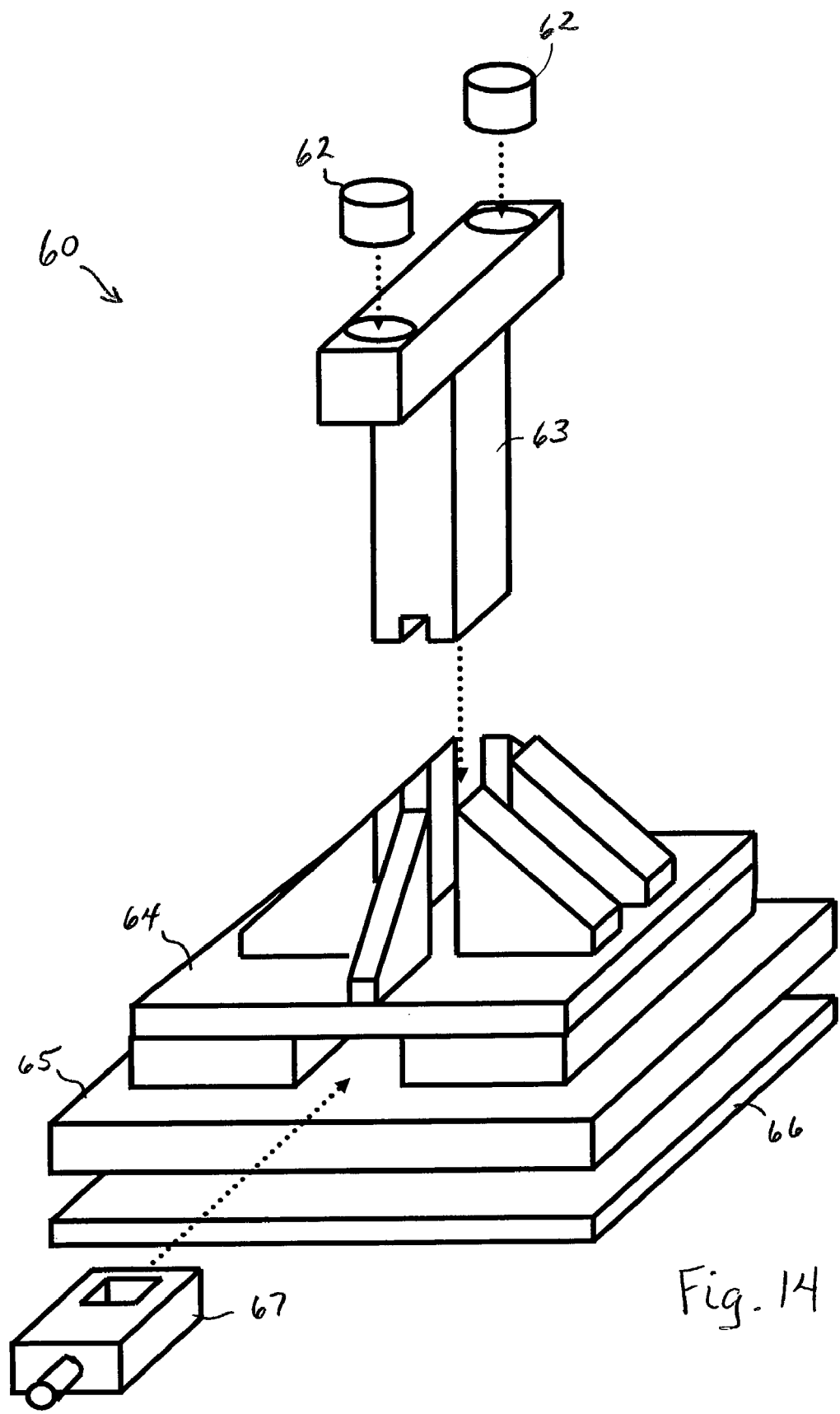

FIG. 14 representatively shows a partially expanded testing stand system for determining conformability and gap-protrusion area.

FIG. 15 representatively shows a ram member of the testing stand system.

FIG. 15A shows a representative side view of the ram member of FIG. 15.

FIG. 15B shows a representative top view of the ram member of FIG. 15.

Figure 16B:
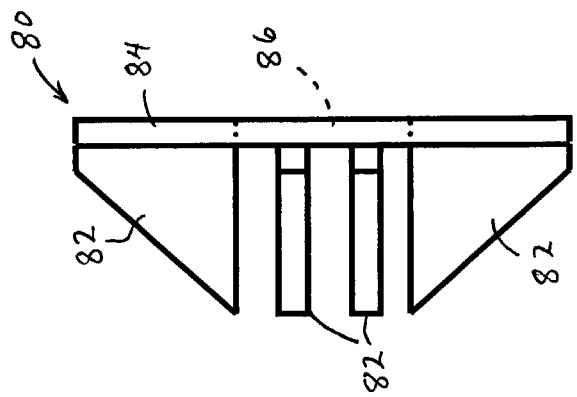
Figure 16:
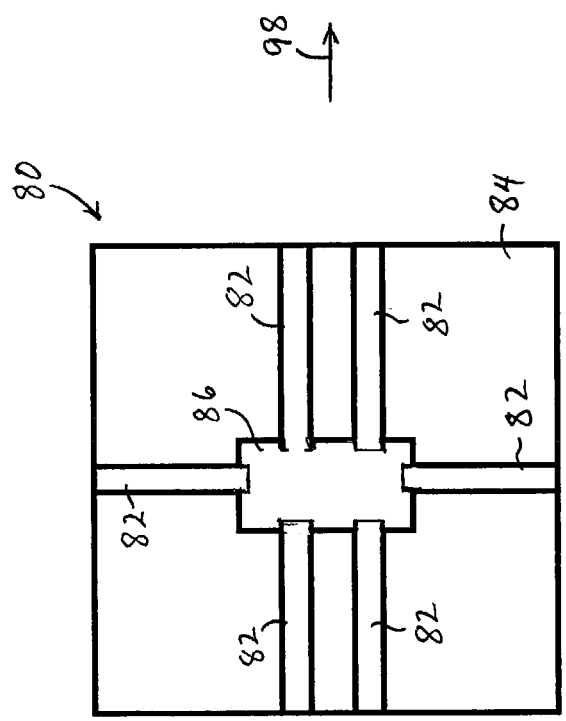

FIG. 16 representatively shows a top view of a ram support member of the testing stand system.

Figure 16A:
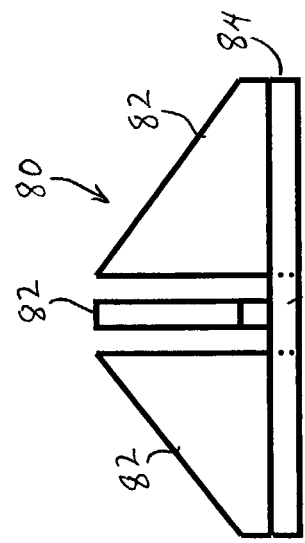

FIG. 16A shows a representative side view of the ram member of FIG. 16.

FIG. 16B shows a representative end view of the ram member of FIG. 16.

FIG. 17 representatively shows a top view of a leveling-base member of the testing stand system.

FIG. 17A shows a representative side view of the ram member of FIG. 17.

FIG. 17B shows a representative end view of the ram member of FIG. 17.

Figure 18:
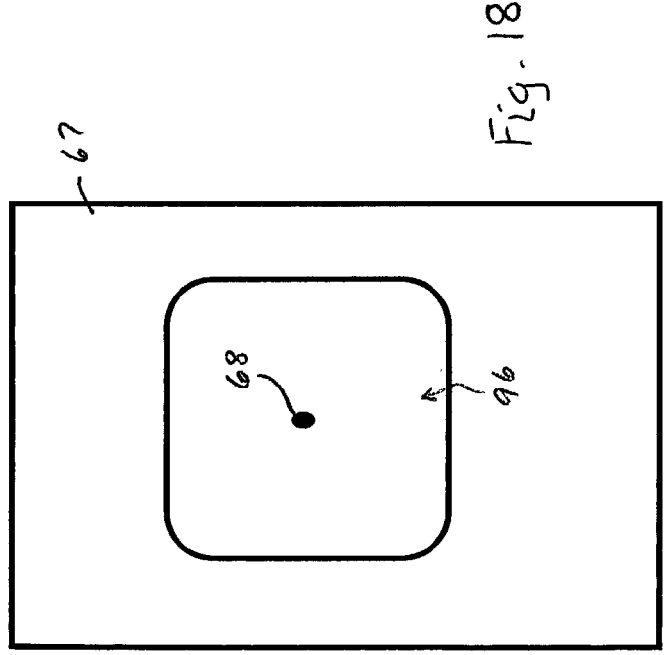

FIG. 18 representatively shows a top view of a sample holder of the testing stand system.

Figure 18A:
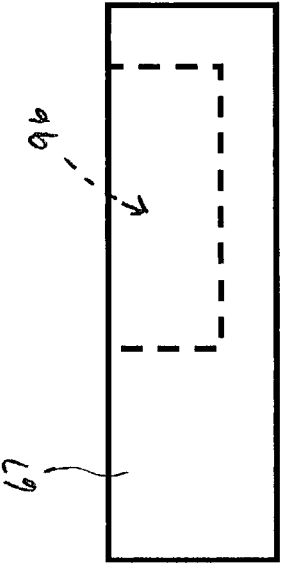

FIG. 18A shows a representative side view of the sample holder of FIG. 18.

Figure 18B:
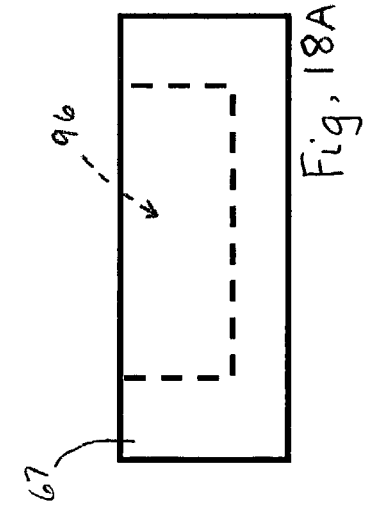

FIG. 18B shows a representative end view of the sample holder of FIG. 18.

Figure 19:
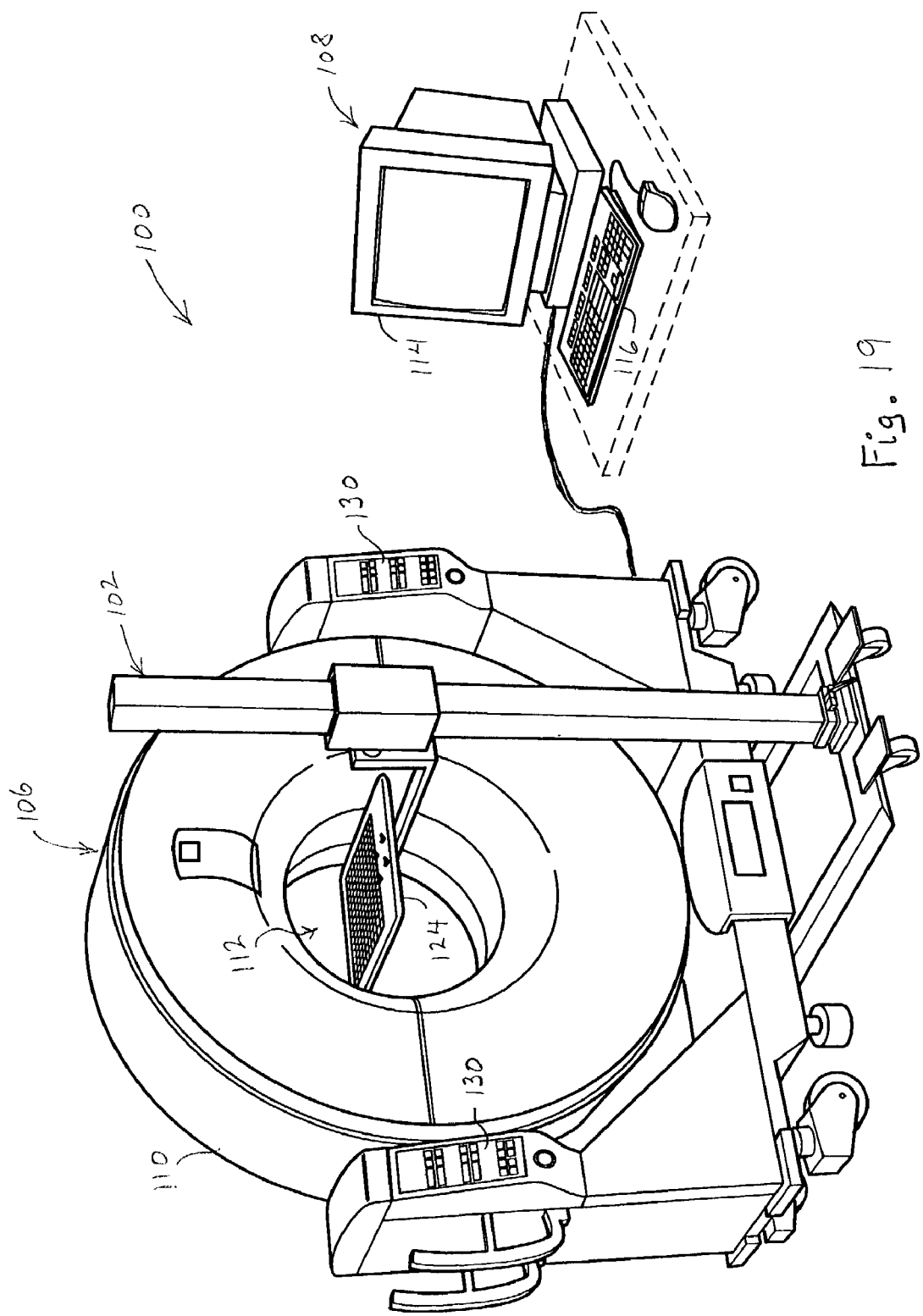

FIG. 19 shows a representative CT (computerized tomography) scanner system.

Figure 19A:
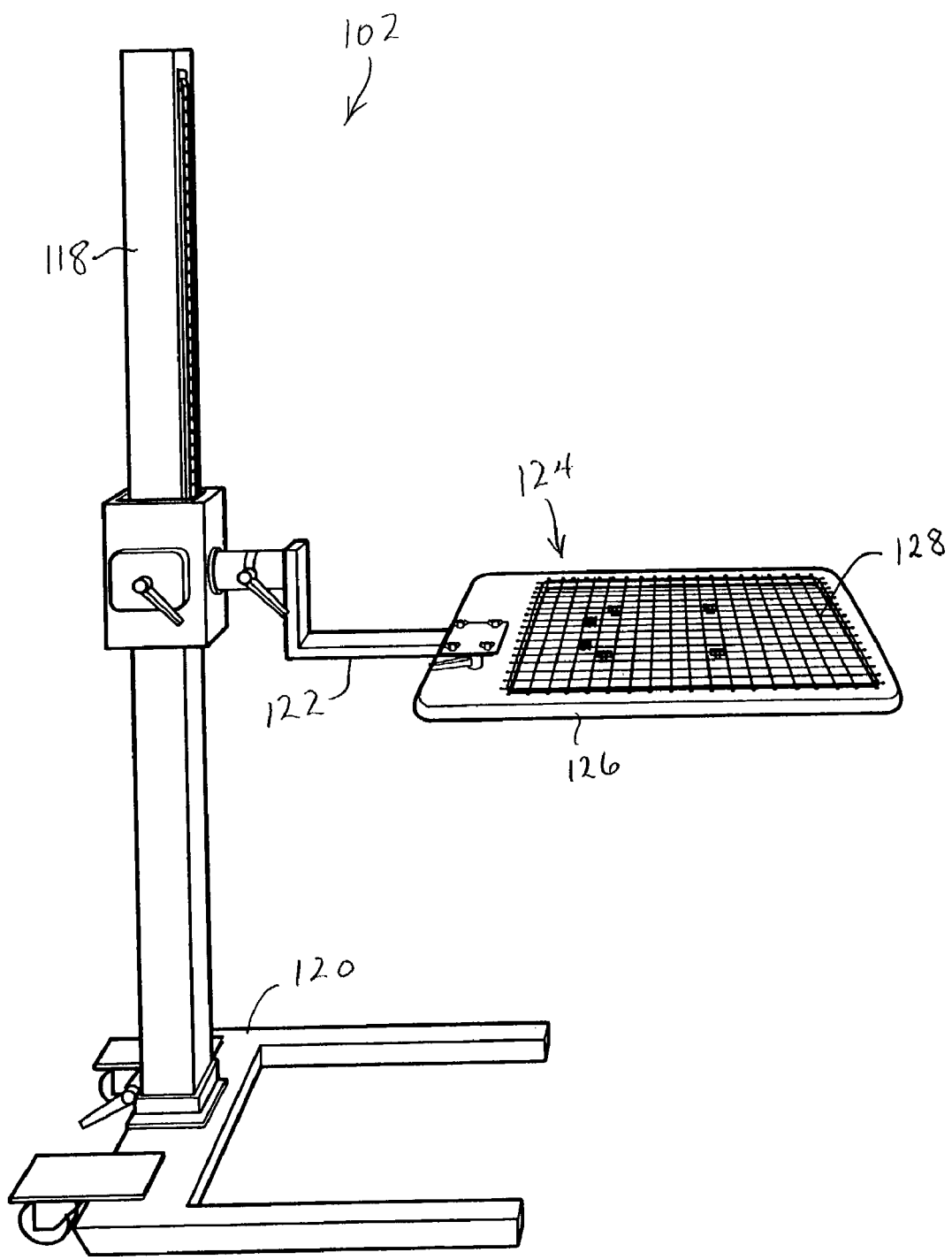

FIG. 19A shows a representative support device for positioning a sample holder and sample in the CT scanner.

Figure 20:
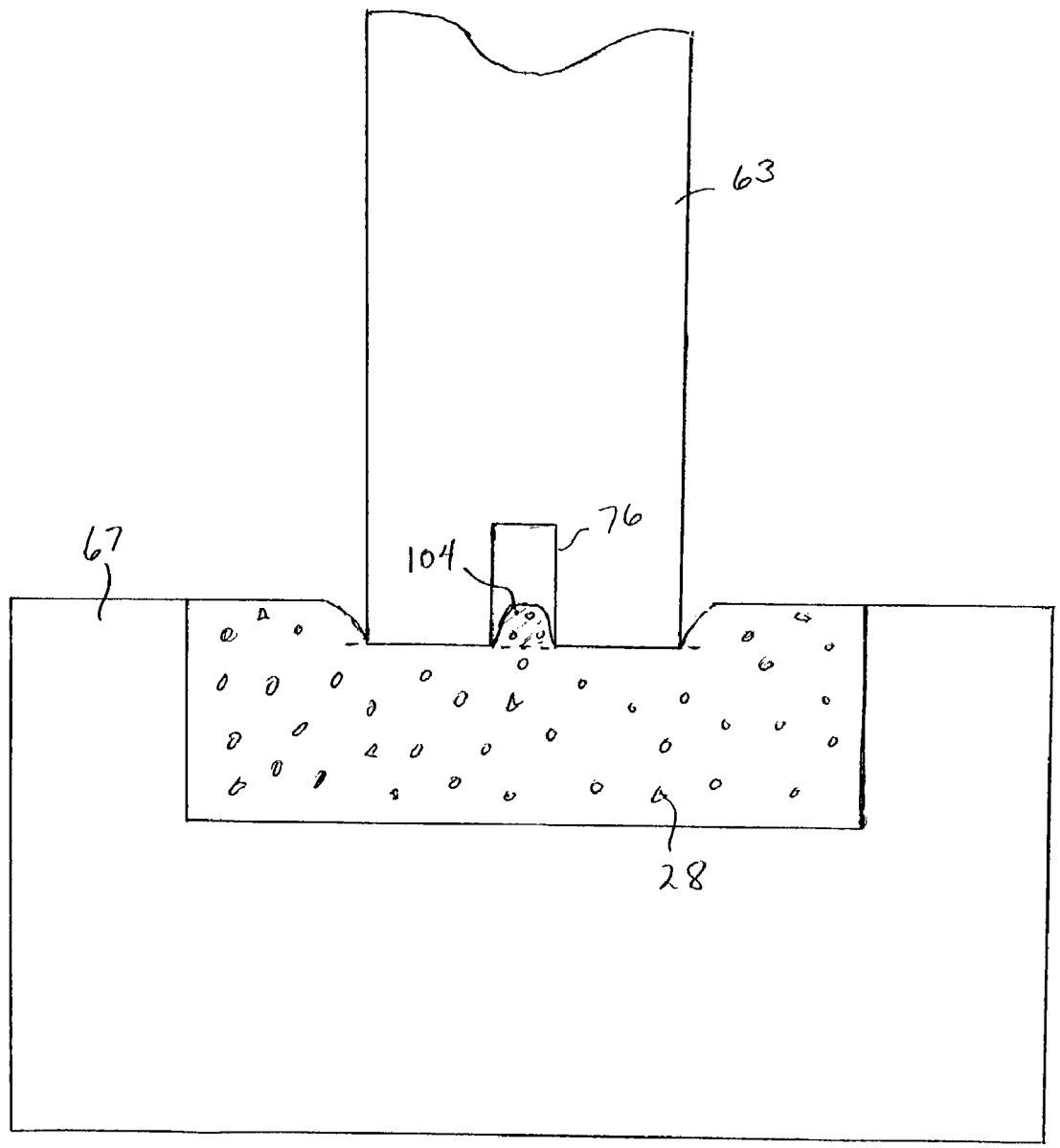

FIG. 20 shows a schematic view of a representative CT image illustrating a cross-sectional area of particulate material that has protruded into the channel-gap region of a testing apparatus.

Figure 21:
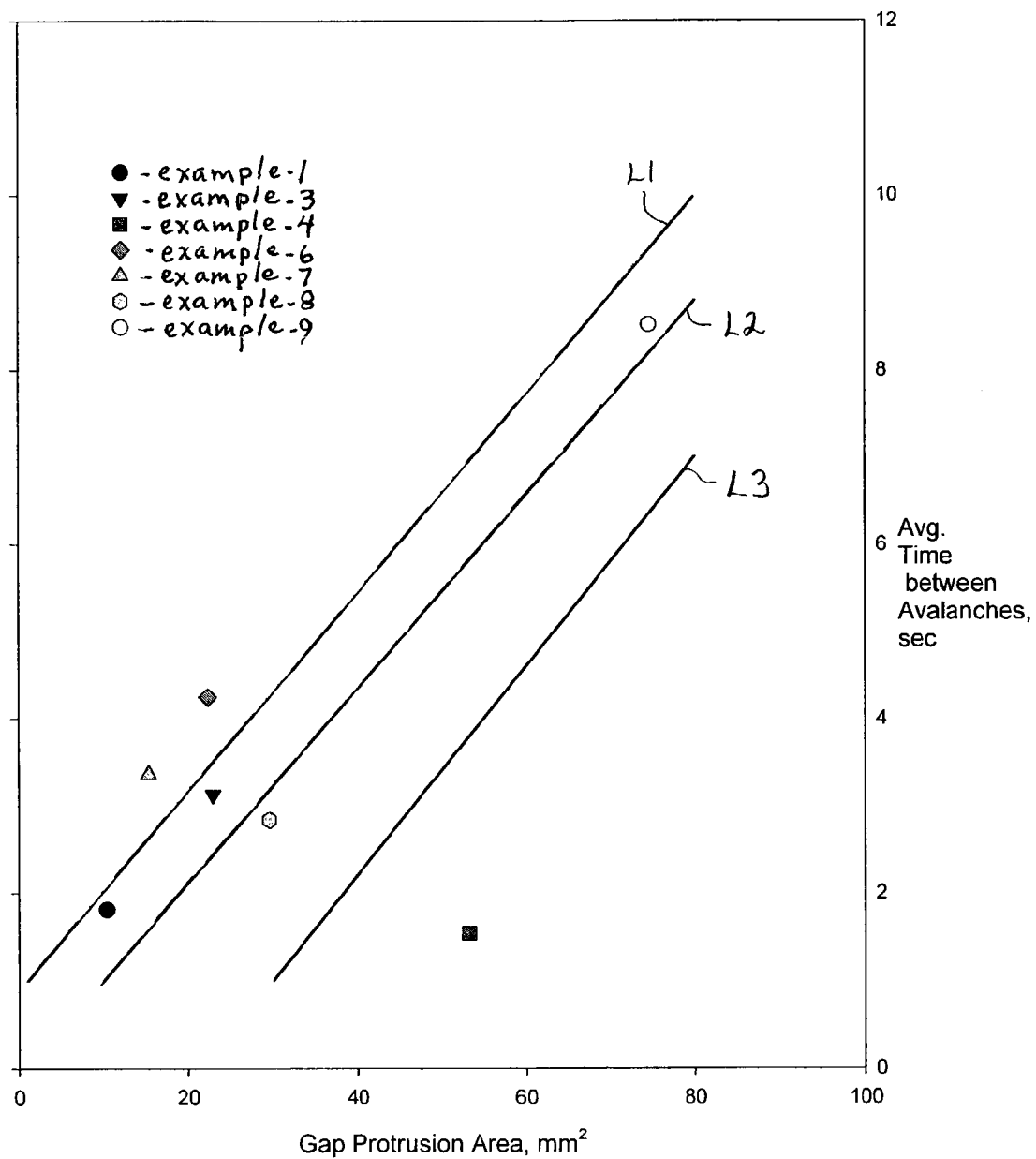

FIG. 21 shows a graphical plot of the values of avalanche-time and gap-protrusion area that were obtained from samples of particulate material to determine conformance capability.

DETAILED DESCRIPTION

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The adsorbent materials employed with the present invention can include any operative adsorbent particles, alone or in combination with other treatments or additives. Examples of additives can include fibers, or other particulate materials which may be composed of absorbent or substantially non-absorbent materials. The absorbent materials may, for example, include poly(acrylate) superabsorbent particles. The substantially nonabsorbent materials may, for example, include beads or other particulates of a selected polymer. In particular configurations, the nonabsorbent particles can help provide a desired level of bulk volume to the various configurations of the present invention. The adsorbent particles can also include particulates that are treated with an additive which is a surface modifying agent.

By the terms "particle," "particles," "particulate," "particulates" and the like, it is meant that the adsorbent material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the general properties of the red blood cells.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the personal care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be absorbed by the absorbent article, and the backsheet is substantially impermeable or otherwise operatively impermeable to the intended liquids. The absorbent articles may also include other components, such as liquid wicking layers, liquid distribution layers, barrier layers, and the like, as well as combinations thereof. Disposable absorbent articles and the components thereof, can operate to provide a body-facing surface and a garment-facing surface. As used herein, "body-facing surface" means that surface of the article or component which is intended to be disposed toward or placed adjacent to the body of the wearer, while the "garment-facing surface" is on the opposite side, and is intended to be disposed toward or placed adjacent to the wearer's undergarments when the disposable absorbent article is worn.

With reference to FIGS. 1 through 4, the present invention can provide a body-conformance system 22 which can be positioned at least operatively proximate a bodyside surface of a selected article 20. The body conformance system can include at least one liquid-permeable, flexible containment layer 24, and an operative quantity of substantially free-flowing particulate material 28 which is operatively constrained by the flexible containment layer. In a particular aspect, the substantially free-flowing particulate material can have a distinctive avalanche-time. In another aspect, the particulate material can have a distinctive retention capacity. A further aspect can include a containment layer which is configured to provide the operative containment of the particulate material and a sufficiently high rate of liquid flow-through. Yet another aspect of the invention can include a containment layer which is configured to provide a selected intake-handling time. In still a further aspect, the invention can be configured to provide a distinctive gap-protrusion area 104 (e.g. FIG. 20).

In its various aspects and features, alone or in combination, the present invention can provide an article and system that can more effectively provide an enhanced body conformance and improved fit. The configurations of the invention can help reduce the occurrence of irritating pressure-points and can help provide improved comfort to the wearer. An article with increased body conformance can provide increased comfort, greater discretion and better protection. The article better conforms to the shape of the wearer's body, provides less gapping between the body and the article, and provides more overall comfort due to the improved fit. The article can fit closer to the wearer's body to better capture liquids, to help provide improved retention of liquid, and to reduce the chance of leakage. Desirably, the article and system of the invention can provide such improved performance in a personal care article, such as an absorbent, personal care article. In a particular aspect, the present invention can provide an article and system that can more effectively provide such improved performance in a personal care article that has been configured to hold liquid-complexes, such as complex body-liquids.

The substantially free-flowing particulate materials employed with the present invention can be appropriately combined with an operative containment system or structure to provide the desired body-conformance system 22. In a particular aspect, the particulate material 28 can be held or otherwise carried by or within a suitable containment system or mechanism. Any system or mechanism which is capable of holding or otherwise carrying the selected adsorbent materials, and is capable of being operatively located in a disposable absorbent article, can be employed in the present invention. Many such containment systems or mechanisms are known to one skilled in the art. For example, the containment structure may include a fibrous matrix, such as an airlaid or wet laid web of cellulosic fibers, a carded web, a hydroentangled web, a meltblown web of synthetic polymeric fibers, a spunbonded web of synthetic polymeric fibers, a bicomponent spunbond web, a coformed matrix comprising cellulosic fibers and fibers formed from a synthetic polymeric material, airlaid heat-fused webs of synthetic polymeric material, open-celled foams, or the like, as well as combinations thereof.

Figure 1:
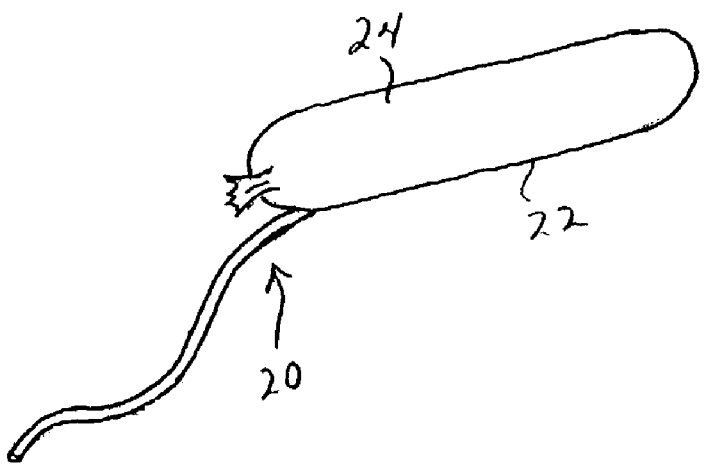
FIG. 1 shows a representative tampon article which incorporates the body-conformance system of the invention.
Figure 2:
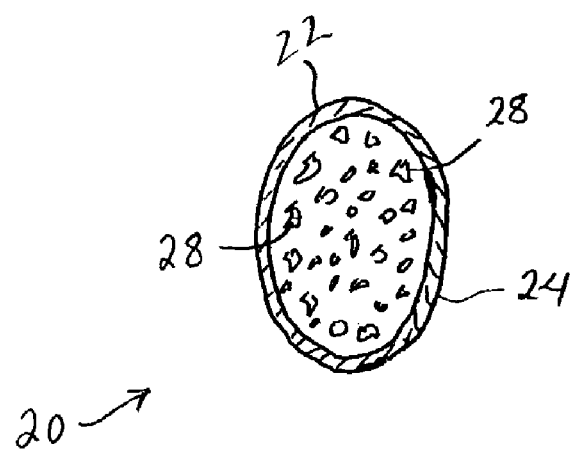
FIG. 2 shows a representative end-wise view of a transverse cross-section through a tampon article which incorporates the system of the invention.
Figure 2A:
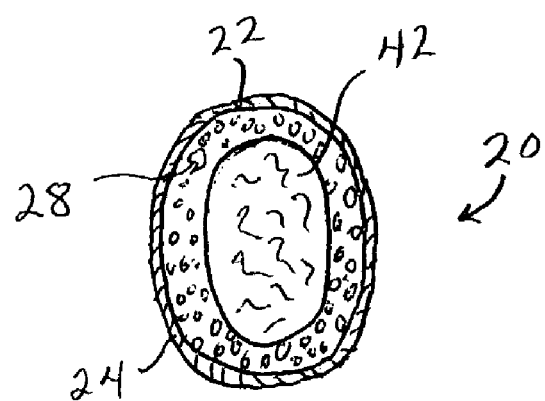
FIG. 2A shows a representative end-wise view of a transverse cross-section through another tampon article which incorporates the system of the invention.

The body-conformance system 22 can include at least one flexible containment layer 24, and the containment layer can be provided by any operative material. For example, the containment layer may be an individual material or a composite material. The containment layer 24 is sufficiently flexible to provide comfort and conformability, and can be configured to help direct bodily exudates away from the body of the wearer and toward a selected retention portion 42 of the article (e.g. FIGS. 2A, 5, 6). In a desired feature, the containment layer 24 can be configured to retain little or no liquid in its structure, and may be configured and arranged to provide a relatively comfortable and non-irritating surface next to the body tissues of a female wearer. The containment layer may be generally liquid-impermeable, but desirably is operatively liquid-permeable. The containment layer 24 can be constructed of any material which is also easily penetrated by bodily fluids contacting its surface. For example, the containment layer can include a woven fabric, a nonwoven fabric, a carded web, a hydroentangled web, a meltblown web, a bicomponent spunbond web, a polymeric film that has been configured to be operatively liquid-permeable, or the like, as well as combinations thereof. Examples of suitable materials for constructing the containment layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A particular example of a suitable containment layer material can include a bonded-carded-web composed of polypropylene and polyethylene. Other examples of suitable materials are composite materials of a polymer and a nonwoven fabric material. The composite materials are typically in the form of integral sheets generally formed by the extrusion of a polymer onto a web of spunbond material. The liquid-permeable containment layer 24 may optionally contain a plurality of apertures (not shown) formed therein which can increase the rate at which bodily liquids can move through the thickness of the containment layer.

The containment layer 24 may also include a physiologically hydrous material. As used herein, the term "physiologically hydrous" is intended to connote a cover material which can maintain a suitably moist interface between the absorbent article 20 and any contacting body-tissues of the wearer that are ordinarily moist. For example, such moist-tissue regions are present in the vulvovaginal area of the female anatomy. The physiologically hydrous cover material can provide a desired level of comfort when disposed within the selected, moist-tissue environment of the wearer. Thus, while the containment layer may not be "hydrous" in the classic sense, inasmuch as the containment layer will be substantially dry prior to use on the wearer, the containment layer 24 can maintain, or at least can avoid excessive interference with, a hydration level or balance that is desired within the ordinarily-moist body tissue.

Physiologically hydrous materials are, for example, described in detail in U.S. Pat. No. 4,846,824 to F. Lassen et al., and in U.S. Pat. No. 5,891,126 to Osborn III et al. The entire disclosures of these documents are incorporated herein by reference in a manner that is consistent herewith.

The containment layer 24 can also have at least a portion of its bodyside surface treated with a surfactant to render the containment layer more hydrophilic. The surfactant can permit arriving bodily liquids to more readily penetrate the containment layer. The surfactant may also diminish the likelihood that the arriving bodily liquids, such as menstrual fluid, will flow off the containment layer rather than penetrate through the containment layer. In a particular configuration, the surfactant can be substantially evenly distributed across at least a portion of the upper, bodyside surface of the containment layer 24 that overlays an upper, bodyside surface of a selected retention portion of the article. In other configurations, the surfactant may be applied in a selected pattern, such as provided by a regular or irregular array of dots or stripes.

The containment layer 24 may be maintained in secured relation with other components of the article by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the selected component with portions of the adjacent surface of the containment layer, or fusing at least portions of the adjacent surface of the containment layer to portions of the adjacent surface of the selected component.

The containment layer 24 can typically be positioned at or operatively near at least one body-contacting surface of the article. Additionally, the containment layer can be configured to partially or entirely surround and enclose the substantially free-flowing particulate material 28.

The substantially free-flowing particulate material employed in the article or system of the invention can include any operative particulate material. In desired arrangements, the substantially free-flowing particulate material can include particles of an adsorbent material, and the particulate adsorbent material can be configured to include one or more distinctive parameters. While a wide variety of adsorbent materials are known, the present invention can incorporate a distinctive selection of the adsorbent materials that are suitable for use in the handling of complex liquids such as, for example, blood, menses, loose feces, vaginal discharges, nasal discharges and the like, as well as combinations thereof.

Adsorbent materials suitable for use in the handling of complex liquids desirably are substantially wettable or hydrophilic with respect to the complex liquids, thus allowing the complex liquids to spread over the surface of the adsorbent materials. In addition, the adsorbent materials employed in the present invention are desirably in particle form and substantially insoluble in the complex liquids. It is further desired that the adsorbent materials of the present invention be substantially inert, and neither substantially soften nor substantially swell during adsorption. Any such suitable adsorbent material desirably has a high surface area relative to its weight, as determined by an appropriate measuring method, such as gas adsorption, cetyltrimethyl ammonium bromide adsorption, or mercury intrusion porosimetry. These, as well as other suitable methods, are described in detail in *Analytical Methods in Fine Particle Technology*, authored by Paul A. Webb and Clyde Orr, and published by Micromeritics Instrument Corporation, Norcross, Ga.

Adsorbent materials suitable for use in the present invention include, but are not limited to, organic materials, inorganic materials and combinations thereof. Suitable materials include, for example, activated carbon, silicates, granulated silica, perlite, vermiculate, granulated clay, glass beads, metal oxides, zeolites, carbonates, phosphates, borates, aerogels, or the like. Other suitable materials can include, for example, cellulosic materials, cellulosic nits, cellulose particles, starches, chitins, alginates, synthetic polymers, or the like. In addition, any operative combination of the adsorbent materials may be employed.

The adsorbent material may optionally be treated with a surfactant or other surface-modifying agent prior to incorporation into any containment means or mechanism. Many materials are useful in this application, for example soluble proteins, starch, chemically-modified starch, sulfonated alkyl and aryl compounds, ethoxylated alcohols and amines, polyamides and their derivatives, polysaccharides and their derivatives, polyethylene glycols and their derivatives, betaines and other zwitterionic compounds, and silyl compounds, as well as combinations thereof. Appropriate articles and techniques for incorporating the adsorbent material into the desired article are well known to one skilled in the art.

When used in a feminine hygiene product, the adsorbent material of the present invention can have a certain desirable distribution of pore sizes. In a bed of adsorbent particles, the pores can be provided by the spaces between particles (interstitial spaces), as well as an internal pore structure of the particles themselves. These interstitial spaces are linked to form what can be considered as a network of interstitial spaces. When a liquid moves into or through a bed of particles, the liquid generally moves through these interstitial spaces. These interstitial spaces that the liquid moves through can also be referred to as interstitial pores.

Since the walls of an interstitial pore are the surfaces of the particles themselves, the shape and size of the interstitial pores are usually determined by the particles themselves. Varying the size of the particles by varying their average dimensions or the distribution of their dimensions, varies the shape and size of the interstitial pores. Interstitial pores play a significant role in the intake rate and retention of a complex liquid by adsorbent particles.

Adsorbent materials suitable for use desirably have an acceptable rate of intake with respect to complex liquids. This acceptable rate of intake can be achieved through a heterogeneous distribution of pore sizes, and as previously discussed, a combination of particle sizes can provide an appropriately heterogeneous distribution of pore sizes. The pore sizes can suitably range from about 1,000 microns (micrometer) to about 0.2 microns (µm), where pore sizes between about 1,000 µm to about 100 µm can be primarily useful for the rapid intake and distribution of a complex liquid, and pore sizes between about 100 µm and about 0.2 µm can be primarily useful for the separation and retention of the components of a complex liquid.

The pore size distribution may be measured by the Capillary Tension Test identified in the TESTING section of the present disclosure, or by employing mercury porosimetry. Mercury porosimetry can be conducted by a commercially available testing laboratory, such as Micromeritics, a business having offices located in Norcross, Ga., U.S.A., or Quantachrome, a business having offices located in Syosset, N.Y., U.S.A. For example, mercury porosimetry data regarding pore size, pore volume and pore size distribution can be obtained from Micromeritics Instrument Corp., One Micromeritics Dr., Norcross, Ga. 30093 U.S.A. The testing can include Macro and Meso Volume/Size Distribution by Mercury Intrusion Porosimetry, Test No. 005-65000-31, and test samples can be run on Micromeritics Instrument Corp.'s AutoPore Mercury Porosimeter, Unit 750.

Adsorbent particles are capable of retaining liquid in the interstitial pores or spaces between the particles as well as in the internal pores of the individual particles. It is desirable that the pores of an individual particle are accessible from the surface of the particle to adsorb the liquid. Liquid is capable of entering the internal pore volume of an individual particle through capillary forces. The addition of internal pores allows the liquid or liquid portion of the complex liquid to be retained by capillary force within the internal pores. This creates a dry feeling against the body, and diminishes the amount of free liquid in the bed of adsorbent particles. Consequently, the adsorbent particles can help minimize rewet. Suitable adsorbents can have a range of internal pore sizes from about 100 µm to about 0.2 µm to adsorb different sized components of a complex liquid and thus minimize liquid rewet as measured by the Rewet and Retention test methods described herein.

Where a large number of small pores are present, the liquid-handling properties of the structure can be affected. For example, the liquid component of a complex liquid can be removed too rapidly. As result, the remaining components of the complex liquid may not be adequately distributed or spread. In the case of menses, such remaining non-liquid components are composed mostly of solids, such as human tissue and cells. To address this situation, the invention can incorporate a feature wherein the volume of pores having a pore size less than 1 micron is not more than a maximum of about 2 percent of the total pore volume.

Based on the foregoing, adsorbent materials suitable for use in the present invention have the following parameters: wettable, stable when exposed to aqueous liquid, suitable interstitial pore size distribution for acceptable intake rate, and suitable internal pore size distribution for desired retention. Additionally, the adsorbent materials can be configured to help provide the desired body-conformance.

In the various arrangements of the present invention, other parameters of the adsorbent material may be desirable. For instance, when the complex liquid is menses and the adsorbent material is used in feminine hygiene products, the adsorbent materials employed with the present invention can have a particle size of between about 1,000 to about 100 microns (µm); and, more desirably, between about 850 to about 150 microns. It has been found that particles of adsorbent material having a size above about 1,000 microns are generally, readily perceptible to the wearer of any containment or carrier structure that supports the adsorbent materials of the present invention. It has also been found that particles of adsorbent material having a size below 100 microns are difficult to contain within any containment mechanism that readily allows complex liquids to penetrate through the containment mechanism to the adsorbent materials. It should be understood that the particles of adsorbent material falling within the range identified herein may comprise individual porous particles, or may be agglomerated particles which each agglomerated particle comprising a plurality of smaller particles composed of one or more types of adsorbent materials.

Another desirable specific parameter is retention capacity, which is expressed as the weight, (e.g. in grams) of the liquid retained, divided by the weight (e.g. in grams) of the adsorbent employed. Accordingly, the adsorbent retention capacity can be expressed in the units of grams of retained liquid-per-gram of retention material (g/g). For example, where the complex liquid is menses and the adsorbent material is incorporated into a feminine hygiene product, the capacity can be expressed in terms of grams of menses simulant per gram of adsorbent material, and can be determined by employing the Retention Capacity test identified in the present disclosure. The complex-liquid retention capacity of the adsorbent can be between about 1 and about 15 g/g; alternatively, between about 2 and about 8 g/g; and finally, alternatively, between about 2 and about 6 g/g. It is believed that adsorbent materials having lower retention capacities than 2 g/g would require the use of such large amounts of adsorbent material that users may find the feminine hygiene product to be excessively heavy. The complex liquid retention capacity can be estimated by summing the amount of pore volume between about 100 and about 0.2 microns in diameter. The pore volume can be determined, for instance, by capillary tension or mercury intrusion porosimetry. The complex liquid retention capacity can be limited by the strength of the pore wall material.

As previously mentioned, a mixture of particle sizes can be desirable to improve liquid intake and retention. Sufficient interstitial pores between particulates are needed so that menses can rapidly enter into the bed of adsorbent particles and be distributed between the particulates. This property may be controlled with the particle size distribution of the adsorbent material. Generally, a broad particle size distribution is desired. A broad particle size distribution is used herein to describe a distribution having a standard deviation greater than 25 percent of the mean value.

The inventors have also found that a combination of pore sizes can be effective at adsorbing a complex liquid. A bi-modal or multi-modal particle size distribution can be particularly desirable for producing a combination of pore sizes that can be desirable for enhancing the intake, distribution and retention of a complex liquid. One manner of achieving a desired pore size distribution can be to combine adsorbent particles of various sizes.

The adsorbent or other substantially free-flowing particulate material can be distinctively configured for use in a method or system for increasing body-conformance. In a particular aspect, the substantially free-flowing particles can readily conform to the contours of the wearer's body as the wearer moves. In another aspect, the particles can freely rearrange to operatively provide the desired body-conformance. In further aspects the operatively free movement, and the operatively free rearrangement of the particles can occur when the particles are dry and/or when the particles are wet.

In a particular feature, the method or system can include a substantially free-flowing particulate material which exhibits a selected avalanche-time. Desirably, the particulate material can be configured to provide an avalanche-time of not more than a maximum of about 10 seconds (sec) between avalanches. The avalanche-time can alternatively be not more than about 5 sec, and can optionally be not more than about 3 sec. A further configuration can include particulates that have an avalanche time of not more than about 2 sec. In still another aspect, the avalanche time can be at least a minimum of 0.1 sec. If the avalanche-time does not have the desired values, there can be poor fluid distribution, and/or an inefficient or partial use of the particulates. Additionally, there can be an excessive clumping of the particulates which may decrease product comfort and degrade functional intake properties. The particulates may also be insufficiently able to move relative to one another to provide the desired level of body conformance.

The avalanche-time can be determined by employing the Avalanche-Time Test Method set forth in the TESTING section of the present disclosure.

In another feature, the substantially free-flowing particulate material in the body-conformance system can exhibit a selected retention capacity. Desirably, the retention capacity can be at least about 1 gram of menses-simulant per gram of the particulate material (1 g/g menses simulant), and can alternatively be at least about 2 g/g. In another feature, the retention capacity can be up to about 15 g/g. The retention capacity can alternatively be not more than a maximum of about 8 g/g, and can optionally be not more than about 5 g/g to provide desired benefits. If the retention capacity is outside the desired ranges, the product can have excessive flow-back or excessive rewet characteristics. Additionally, the product may have inadequate absorbent capacity, and may be suitable only for light-flow occasions instead of for medium-flow to heavy-flow occasions.

The retention capacity can be determined by employing the Method for Determining Retention Capacity that is identified in TESTING section of the present disclosure The article and body-conformance system can be configured to provide a selected intake-handling time. In a desired configuration, the substantially free-flowing particulate material can be configured to provide a selected intake-handling parameter. A particular feature of the invention can be arranged to provide an intake-handling time of not more than a maximum of about 120 sec per 2 mL of menses-simulant at a flow rate of 250 mL/hr. The intake-handling time can alternatively be not more than about 60 sec, and can optionally be not more than about 30 sec to provide improved performance.

If the intake-handling time is excessive, there can be premature leakage or an inadequate ability to handle and absorb gushes of liquid. Additionally, liquid may pool on the surface of the product and cause excessive discomfort. The intake-handling time can be determined by employing the Intake Rate and Rewet Test that is identified in the TESTING section of the present disclosure.

In another feature, the article and the particulate material of the body-conformance system 22 can provide a selected "gap-protrusion area" 104 (e.g. FIG. 20). In particular aspects, the gap-protrusion area can be at least a minimum of about 7 mm$^2$. The gap-protrusion area can alternatively be at least about 8 mm$^2$, and can optionally be at least about 9 mm$^2$ to provide improved performance. A further aspect can include particulate material that provides a gap-protrusion area of at least about 15 mm$^2$. In other aspects, the gap-protrusion area can be up to a maximum of about 80 mm$^2$. The gap-protrusion area can alternatively be up to about 75 mm$^2$, and can optionally be up to about 70 mm$^2$ to provide improved effectiveness.

If the gap-protrusion area value is outside the desired values, the particulate material in the body-conformance system may not have a sufficient ability to deform when the particulate material is subjected to an applied pressure.

The gap-protrusion area can be determined by employing the Gap-Protrusion Area Test Method that is described in the TESTING section of the present disclosure.

A further feature of the article of the invention can be provided by a body-conformance, particulate material which has a particular combination of avalanche-time and gap-protrusion area. In a particular aspect, the particulate material can have an avalanche-time of less than about 2 sec, and a gap-protrusion area which is less than about 15 mm$^2$. In another aspect, the avalanche-time can be less than about 2 sec, and the gap-protrusion area can be within the range of about 8 mm$^2$ to about 15 mm$^2$.

In still another arrangement, the particulate material can have a gap-protrusion area which is at least about 15 mm$^2$ and an avalanche-time of more than about 2 sec. The gap-protrusion area can be up to about 80 mm$^2$. Additionally, the avalanche-time can be up to about 10 sec, and can optionally be up to about 4 sec to provide improved performance.

The substantially free-flowing particulate material in the body-conformance system may include substantially nonabsorbent material, and may also include absorbent material. The absorbent particulate material can, for example, include cellulose granules or bundles ("nits"), superabsorbent particles, coated superabsorbent particles, or the like as well as combinations thereof. For example, the particulate, absorbent material can be a FAVOR 880 polyacrylate superabsorbent material available from Stockhausen, a business having offices located in Greensboro, N.C., U.S.A.

It should be noted that the present invention is not limited to the use of only one of the adsorbent materials or other particulate materials disclosed herein, but can also include mixtures or other combinations of two or more materials. As previously indicated, the substantially free-flowing material is in particle form; consequently, use of the phrase "particulate material" throughout the specification and claims includes a quantity having one or more individual particles of material, or a quantity having agglomerations which include two or more particles of the same or different materials.

The adsorbent material, and in desired arrangements, the substantially free-flowing particulate material, can be present in the containment mechanism or carrier structure in an amount which is within the range of about 2 to about 100 weight percent (wt %); alternatively, about 20 to about 100 wt %; alternatively, about 30 to about 100 wt %; alternatively, about 40 to about 100 wt %; alternatively, about 50 to about 100 wt %; alternatively, about 60 to about 100 wt %; alternatively, about 70 to about 100 wt %; alternatively, about 80 to about 100 wt %; and alternatively, about 90 to about 100 wt % based on the total weight of the adsorbent and/or other material that is operatively combined with the containment mechanism or carrier structure.

In particular arrangements of the present invention, the article can provide another carrier structure which includes two or more, separately provided layers of material which are joined to form an operative pocket region configured to contain the adsorbent or other particulate material. One or more of the layers can be suitably formed from any material capable of containing the adsorbent or other particulate material, and the material can include woven and nonwoven materials such as fabric materials which include airlaid fibers, wet laid fibers, meltblown fibers, spunbonded fibers, coformed fibers, binder fibers (such as bicomponent fibers) and the like, as well as combinations thereof. The layers of material can be joined to form a pocket by a suitable securement mechanism, such as heat fusion, sonic bonding, adhesives (such as water-soluble or water-sensitive adhesives, latex adhesives, hot melt adhesives, or solvent-based adhesives) and the like, as well as combinations thereof. Clearly, any of a wide variety of materials may be employed to form the two layers, and any of a wide variety of securement techniques may be employed to join the two layers together to form the pocket. The adsorbent or other particulate material can be present in each pocket in an amount within in the range of about 2 to about 100 wt %; alternatively, about 20 to about 100 wt %; alternatively, about 30 to about 100 wt %; alternatively, about 40 to about 100 wt %; alternatively, about 50 to about 100 wt %; alternatively, about 60 to about 100 wt %; alternatively, about 70 to about 100 wt %; alternatively, about 80 to about 100 wt %; and alternatively, about 90 to about 100 wt % based on total weight of the adsorbent or other particulate material held or otherwise present in the pocket region. In addition to the adsorbent or other particulate material, the pocket may contain a fibrous material or other filler material that does not unacceptably affect the properties of the adsorbent or other particulate material.

In another aspect, the carrier structure or mechanism of the article can include a matrix of fibers, and the adsorbent or other particulate material can be mixed with the fibers of the matrix. The adsorbent or other particulate material can be present in the mixture of fibers and adsorbent material in an amount of from about 20 to about 95 weight percent; alternatively, about 30 to about 85 weight percent; and alternatively, about 50 to about 75 weight percent based on total mixture weight.

Any fibers capable of containing an adsorbent or other particulate material and of forming a composite when in combination with the adsorbent or other particulate material are believed suitable for use in the present invention. It is often preferred that the fibers are hydrophilic. As used herein, a fiber or other material can be considered to be "hydrophilic" when it possesses a contact angle of water in air of less than 90 degrees. For the purposes of the present disclosure, contact angle measurements can be determined as set forth by Good and Stromberg in "*Surface and Colloid Science*", Vol. 11 (Plenum Press, 1979).

Fibers suitable for use in the present invention include cellulosic fibers such as wood pulp fluff, cotton, cotton linters, rayon, cellulose acetate, and the like, as well as synthetic polymeric fibers. The synthetic polymeric fibers may be formed from inherently hydrophilic polymeric materials or may be formed from inherently hydrophobic polymeric materials (water in air contact angle of greater than 90 degrees), which fibers are then treated to render at least the outer surface of the fibers hydrophilic. For example, hydrophilic fibers may be formed from an intrinsically hydrophilic polymer such as a block copolymer of nylon, e.g., nylon-6, and a polyethylene oxide diamine. Such block copolymers are commercially available from Allied-Signal Inc. under the trade designation HYDROFIL. Alternatively, the fibers may be formed from an intrinsically hydrophobic polymer such as a polyolefin or polyester which has been surface modified to provide a generally non-fugitive hydrophilic surface. Such surface modified polyethylene is commercially available from the Dow Chemical Company under the trade designation ASPUN wettable polyethylene.

When the hydrophilic fibers are formed by applying a hydrophilic surface treatment to a generally hydrophobic polymer, it may be desirable to employ a generally non-fugitive surface treatment in order to obtain the desired performance.

The synthetic polymeric fibers suitable for use in the present invention may be formed by a melt-extrusion process wherein fibers of a polymeric material are extruded and attenuated to produce fibers having a desired diameter. Alternatively, the fibers may be formed through a spinning process. It is believed that any fiber-producing process known to one skilled in the art can be suitable for use in the present invention.

Fibers suitable for use in the present invention can generally have a length of at least about 1 millimeter. The fibers may have a maximum length approaching infinity. That is to say, the fibers may be essentially continuous such as those fibers formed through a meltblowing process under certain conditions known to one skilled in the art.

Reference to a mixture of fibers and adsorbent or other particulate material is intended to refer to a situation in which the adsorbent or other particulate material is in direct contact with the fibers or is not substantially prevented from migrating into contact with the fibers. Thus, for example, in a multi-layered adsorbent core in which the first layer comprises an airlaid mixture of wood pulp fluff and adsorbent or other particulate material and the second layer comprises only air-laid fluff, only the first layer is considered a mixture of fibers and adsorbent or other particulate material provided, however, that a significant dry migration of the adsorbent or other particulate material between the two layers is substantially prevented. Mechanisms and techniques for preventing such migration are known, and include separating the layers by a tissue wrap sheet, high density fiber layer or similar mechanisms or techniques to prevent a substantial dry migration of the adsorbent or other particulate material between the two layers. The mixture of adsorbent or other particulate material and fibers may be relatively homogenous or relatively non-homogeneous. In the case of a non-homogeneous mixture, the adsorbent or other particulate material may be arranged in a gradient or may be layered with the fibers.

When the containment mechanism or other carrier structure comprises a mixture of fibers and adsorbent or other particulate material, the mixture of fibers and particulate material may be formed in a variety of ways. For example, the mixture may be formed by airlaying or wet-laying the fibers and particulate material, according to processes known in the art, to form batts of the mixture. Airlaying the mixture of fibers and particulate material is intended to encompass both the situation wherein preformed fibers are airlaid with the adsorbent material as well as the situation in which the particulate material is mixed with the fibers as the fibers are being formed, such as through a meltblowing process.

The adsorbent or other particulate materials of the present invention are particularly suitable for use in disposable absorbent articles. In general, the particulate materials may be incorporated into conventional absorbent structures by employing well known techniques. For example, the particulate materials can be incorporated in laminates, in relatively high density cores (i.e., compacted cores, calendered cores, densified cores, etc.), or in relatively low density cores (i.e., not compacted, for example, air-laid cores). The particulate materials of the present invention, however, can provide certain advantages over conventional adsorbent or other particulate materials. In general, when compared to conventional particulate materials, the particulate materials of the present invention demonstrate an improved efficacy in the handling of complex liquids. In particular, the particulate materials of the present invention demonstrate an improved efficacy in the handling of menses. Additionally, the various aspects and configurations of the present invention can provide a more effective control of malodor. As a result, product developers can have the ability to either complement the absorbent systems typically employed in disposable absorbent articles with the various arrangements and configurations of the present invention, or replace certain absorbent systems with the various arrangements and configurations of the present invention.

With reference again to FIGS. 1, 2 and 2A, a representative tampon article can incorporate the body-conformance system of the invention. As representatively shown in FIG. 2, the substantially free-flowing particulate material 28 can be distributed through substantially an entire interior volume of the article. As representatively shown in FIG. 2A, the substantially free-flowing particulate material 28 can be distributed through only a selected part of interior volume of the article. In a particular configuration, the article can include an absorbent retention portion 42, and the particulate material of the body-conformance system can be distributed in at least one layer region that extends completely or partially around a circumferential dimension of the article. Additionally, the one or more layer regions of the body-conformance system can extend completely or partially along a longitudinal, lengthwise dimension of the article. In the representatively shown arrangement, the conformance system has its quantity of substantially free-flowing particulate material 28 located substantially subjacent the flexible containment layer 24, and radially outboard from a cooperating retention portion 42. The retention is positioned relatively inboard from the particulate material 28, and toward a generally central region, as observed along the lateral cross-section of the article.

In a further aspect, the article and body-conformance system can include a containment system or mechanism having a plurality of layers, and the body-conformance system or mechanism may comprise a laminate of at least two layers of material between which the adsorbent material is located and contained. In the representative arrangement illustrated in FIGS. 3 and 4, for example, the body-conformance system 22 can include a first layer and a cooperating second layer. In a particular configuration, a liquid-pervious or liquid-permeable first layer 24 can be configured to provide a bodyside layer of the containment structure, and a second layer 26 can be configured to provide an outward, garment-side layer of the containment structure. The material of the second layer 26 may be the same as, similar to, or different than the material of the first layer 24. Additionally, the second layer 26 may be liquid-permeable or operatively liquid-impermeable, as desired.

In the body-conformance system, each layer of containment material may, for example, be a cloth-like woven or nonwoven fabric, a closed or open-celled foam, a perforated film, an elastomeric material, fibrous webs of material or the like, as well as combinations thereof. When the containment structure or mechanism includes one or more layers of material, the employed combination of material layers should provide a resulting pore structure that is small enough or tortuous enough to provide a containment structure that can operatively confine or otherwise hold at least a majority of the adsorbent material within the containment structure.

The absorbent article 20 can further include a cover layer 30, a backsheet layer 32, and an absorbent core or retention portion 42 which is interposed between the cover layer and backsheet layer.

With reference to FIGS. 5 and 6, a representative absorbent article 20 can include a body-conformance system 22, and a separately provided absorbent retention portion 42. Additionally, the representatively shown article can include a liquid-permeable cover layer 30, and an operatively liquid-impermeable baffle or backsheet layer 32. In the example of the shown arrangement, the flexible containment layer 24 of the body-conformance system 22 can maintain the position of the quantity of free-flowing particulate material 28, and the baffle member can provide an operative garment-side layer of the body-conformance system. The article can further include one or more other components, such as one or more distribution layers 36, and/or one or more article-shaping layers 44. The article-shaping layers may be configured to provide an absorbent component which can be a part of, or can otherwise cooperate with the retention portion. For example, the article can include a resilient, shaping-layer 44 which can be positioned relatively outward from, and immediately adjacent or otherwise operatively proximate a garment-facing surface of the quantity of substantially free-flowing particulate material. The shaping layer can be particularly desirable when the article is configured to be a feminine care article, such as a feminine care pad or liner. A garment-attaching adhesive 46 may be applied to a garment-side surface of the baffle layer, and a release sheet may be superposed over the garment adhesive. Typically, the release sheet is removed immediately prior to placing the article into use. As illustrated in FIG. 5, the retention portion 42 may be located on a bodyside of the body-conformance system 22. As illustrated in FIG. 6, the retention portion can alternatively be located on a garment-side of the body-conformance system.

The bodyside, cover layer 30 can be provided by any material that is operatively liquid-permeable, and may be a composite material. In a particular arrangement, the cover layer can be configured to provide at least a portion of the desired containment structure for the substantially free-flowing particulate material 28. The cover layer 30 can provide comfort and conformability, and can function to direct bodily exudates away from the body and toward the retention portion 42. In a desired feature, the cover layer 30 can be configured to retain little or no liquid in its structure, and can be configured to provide a relatively comfortable and non-irritating surface next to the body-tissues of a female wearer. The cover layer 30 can be constructed of any material which is also easily penetrated by bodily fluids that contact the surface of the cover layer. For example, the cover layer can include a woven fabric, a nonwoven fabric, a polymeric film that has been configured to be operatively liquid-permeable, or the like, as well as combinations thereof. Examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

Suitable cover layer materials can include a bonded-carded-web composed of polypropylene and/or polyethylene, such as has been used as a cover stock for KOTEX brand pantiliners, that can be obtained from Vliesstoffwerk Christian Heinrich Sandler GmbH & Co. KG, a business having an address at Posffach 1144, D95120 Schwarzenbach/Saale, Germany. A more particular example can include a 100% polypropylene bonded carded web having a basis weight of about 22 gsm basis weight. Other examples of suitable materials are composite materials of a polymer and a nonwoven fabric material. The composite materials are typically in the form of integral sheets generally formed by the extrusion of a polymer onto a web of spunbond material. The liquid-permeable cover layer 30 can also contain a plurality of apertures (not shown) formed therein which are intended to increase the rate at which bodily liquids can move through the thickness of the cover layer and penetrate into the other components of the article (e.g. the retention portion 42).

The cover layer 30 may also include a physiologically hydrous cover material. As used herein, the term "physiologically hydrous" is intended to connote a cover material which can maintain a suitably moist interface between the absorbent article 20 and any contacting body-tissues of the wearer that are ordinarily moist. For example, such moist-tissue regions are present in the vulvovaginal area of the female anatomy. The physiologically hydrous cover material can provide a desired level of comfort when disposed within the selected, moist-tissue environment of the wearer, keeping in mind as well the self-evident factor that the absorbent article may be receiving bodily liquids that may be migrating from the wearer to the article. Thus, while not "hydrous" in the classic sense, inasmuch as the cover layer will be substantially dry prior to use on the wearer, the cover layer 30 can maintain, or at least can avoid excessive interference with, a hydration level or balance that is desired within the ordinarily-moist body tissue.

The cover layer 30 can also have at least a portion of its bodyside surface treated with a surfactant to render the cover more hydrophilic. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g. into the retention portion). In a particular configuration, the surfactant can be substantially evenly distributed across at least a portion of the upper, bodyside surface of the cover layer 30 that overlays the upper, bodyside surface of the absorbent.

The cover layer 30 may be maintained in secured relation with the retention portion 42 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover layer 30 typically extends over the upper, bodyside surface of the retention portion, but can alternatively extend around the article to partially or entirely, surround or enclose the retention portion. Alternatively, the cover layer 30 and the baffle layer 32 can have peripheral margins which extend outwardly beyond the terminal, peripheral edges of the retention portion 42, and the extending margins can be joined together to partially or entirely, surround or enclose the retention portion.

In a particular configuration, the backsheet or baffle layer 32 may be configured to provide an operatively liquid-impermeable layer. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the baffle 32 can operatively permit a sufficient passage of air and moisture vapor out of the article, particularly out of an absorbent (e.g. storage or retention portion 42) while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-li.Jungan-mvu.Kongiu-City, Chung cheong nam-do, Republic of South Korea. The baffle material is a breathable film, which is white in color, is dimple embossed, and contains calcium carbonate, $TiO_2$, and polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable baffle material can include a closed cell polyolefin foam. For example, a closed cell polyethylene foam may be employed. Still another example of a baffle material would be a material that is similar to a polyethylene film which is used on commercially sold KOTEX brand pantiliners, and is obtainable from Pliant Corporation, a business having offices located in Schaumburg, Ill., USA.

The retention portion 42 is configured to hold and store the liquids that are directed into the article. The retention portion 42 may include any operative absorbent material, such as cellulosic materials, other absorbent natural-materials, absorbent synthetic-materials, superabsorbent materials and the like, as well as combinations thereof. In a desired feature, the retention portion 42 can exhibit a menses-retention capacity that is within the range of about 1-35 gram menses-simulant per gram of retention material. In another feature, the retention portion 42 exhibits a total retention capacity that can be up to about 100 gram menses-simulant. In a further feature, the retention portion 42 can exhibit a urine-retention capacity that is within the range of about 2-50 gram of synthetic urine (0.9 wt % saline) per gram of retention material (g/g saline). The total holding capacity of the retention portion can be up to about 100 grams of synthetic urine or more. To provide the desired holding capacity for menses and/or synthetic urine, the retention portion may include superabsorbent material.

In the various configurations of the invention, the desired substantially liquid-impermeable or substantially liquid-impervious material has a high-resistance and limited permeability to aqueous liquid, and can have a construction which is capable of supporting a hydrohead of at least about 45 cm of water substantially without leakage therethrough. A suitable technique for determining the resistance of a material to liquid penetration is Federal Test Method Standard FTMS 191 Article 5514, dated 31 Dec. 1968, or a substantially equivalent procedure.

With reference to FIGS. 7 and 8 the body-conformance system 22 may be limited to extend along only a selected portion of the length (y) and/or width (x) dimensions of the article. Alternatively, the body-conformance system can be configured to extend along a total length dimension of the article, and/or may be configured to extend along a total width dimension of the article, as desired. As illustrated in FIG. 8, the article may further include extending tabs, which can be folded around the edges of an undergarment in the crotch region of the wearer to help maintain a desired positioning of the article.

With reference to FIGS. 9 through 9B, the body-conformance system 22 can be configured to cooperate with the retention portion 42 in various alternative arrangements. The body-conformance system can, for example, be partially sunken into a z-directional thickness of the retention portion 42 (e.g. FIG. 9). The body-conformance system 22 can optionally be substantially totally sunken into the z-directional thickness of a selected retention portion 42 (e.g. FIG. 9A). In other arrangements, the body-conformance system may be entirely superposed over, or entirely positioned under the retention portion 42 (e.g. FIG. 9B), as desired.

As representatively shown in FIGS. 10 and 10A, the article can include a plurality of discrete layer regions or strata. The body-conformance system 22 may be incorporated into two or more of the layer regions, and the layer regions that provide the body-conformance system may or may not be in direct contact with one another. With reference to FIG. 10, for example, the article may include three, substantially superposed layer regions 52a, 52b, 52c. The layer regions can extend generally parallel to each other, and may be of different sizes or may be approximately the same size. The particulate material of the body-conformance system may be incorporated into any one of the layer regions, or may be incorporated into all of the layer regions. Alternatively, the particulate material may be incorporated into any other desired combination of two or more of the layer regions. With reference to FIG. 10A, the article can include an array of laterally outboard edge components 54, and the body-conformance system may be selectively incorporated into the edge components With reference to FIGS. 11 and 11A, a representative article can have an array of article components that are distributed along x-y dimensions of the article. The individual components of the array may be absorbent or non-absorbent, as desired. Additionally, the individual components can extend generally continuously along the article, but may be configured to extend discontinuously along the article. The article components may have the form of circular or non-circular rings, and immediately adjacent rings may or may not be arranged to extend generally parallel to each other. The body-conformance system 22 can, for example, be a component which is arranged at a generally medial position with respect to the array of absorbent components (e.g. FIG. 11). Alternatively, the body-conformance system can be arranged in an intermediate position with respect to the array of absorbent components that are distributed along x-y dimensions of the article (e.g. FIG. 11A). Optionally, the body-conformance system can be located at a selected outboard position with respect to the array of absorbent components of the article (e.g. FIG. 11B).

As representatively shown in FIG. 12, an article which incorporates the invention can include a body-conformance system 22 that is configured into any selected combination of individual components, and the components can be distributed and arranged in any operative array of body-conformance components. Each individual body-conformance component can have a discontinuous extent, or a generally continuous extent, and the various body-conformance components can be distributed along any of the various dimensions of the article.

FIG. 13 is a representative, perspective view of a partially sectioned article having a body-conformance system 22 which is configured with a varying contour. In a particular arrangement, the body-conformance system can be configured to provide a regular or irregular array of individual, discrete pocket regions 34. In the illustrated example, the pocket regions are individually formed along a width dimension of the article. The pocket regions may alternatively be individually formed along a length dimension of the article, and may optionally be individually formed along both the width and length dimensions of the article. The illustrated example has pocket regions that are immediately adjacent each other. Alternatively, the pocket regions may be spaced apart by any operative distance or combination of distances. Additionally, the pocket regions may be configured to have any operative shape and volume.

In a particular arrangement, the containment means or mechanism can have at least two layers of material which are operatively joined together to form at least one pocket region or compartment region that contains the adsorbent material. Optionally, the article and body-conformance system can be configured to form a plurality of two or more pocket regions 34 (e.g. FIG. 13). In the various arrangements of the pockets, at least one of the layers of containment material can have an operative level of liquid-permeability, and the liquid-permeable layer may or may not be positioned on a body-side of the body-conformance system. The second layer of material may have a selected level liquid-permeability or may be substantially liquid-impervious, as desired.

It should be readily appreciated that in the various configurations of the invention, the carrier structure can provide at least a portion of a personal care article. The personal care article can, for example, be a wound dressing, a bed pad, an infant diaper, a child's training pant, an adult incontinence product, or the like. In a desired configuration the personal care article can be a feminine care article, such as a garment liner, a sanitary pad, a tampon, a miniform or interlabial device, or the like.

Testing

To determine various parameters that are set forth in the present disclosure, suitable test equipment and procedures are described in detail in PCT Publication WO 00/62826 published Oct. 26, 2000 and entitled ADSORBENTS FOR USE IN HANDLING COMPLEX FLUIDS by William G. Reeves et al. The entire disclosure of this document is incorporated herein by reference in a manner that is consistent herewith. The test methods described in this document include: Intake Rate and Rewet Test Method; Method for Determining Retention Capacity; Capillary Tension Test Method.

Avalanche-Time Test Method

The avalanche-time can be measured by employing an AERO-FLOW Automated Powder Flowability Analyzer, which is available from TSI Incorporated, a business having offices located in Amherst, Mass. 01002-2905 U.S.A. Alternatively, a substantially equivalent system may be employed.

The AERO-FLOW analyzer utilizes deterministic chaos theory to characterize the flow of a sample of particulate material by its avalanching behavior in a rotating cylinder. A designated sample of the particulate material is placed inside a cylinder or drum, and the cylinder is slowly turned at a predetermined rotational speed.

As the cylinder turns, the particulate material is rotated with the cylinder, and the particulate material tends to form a pile of particles which extend along and around the inner surface of the cylinder. The particulate material is carried round by the rotating cylinder until the height of the pile reaches a certain level and the particulate material reaches an unstable position. When this unstable position was reached, the particulate material avalanches and falls down within the cylinder. Accordingly, the particulate material from the top of the pile avalanches down towards the bottom of the pile. Then, the particulate material again rotates along with the cylinder until the particles again reach a point of instability. Thus as the cylinder rotates, the particles will avalanche at a frequency which is dependent on the properties of the particulate material. For a free-flowing particulate material, the time between avalanches will be relatively low. For a cohesive material, the time between avalanches will be relatively greater. Accordingly, the time to avalanche is a function of the flowability of the particulate material. The AERO-FLOW detects the avalanches and determines the time interval between avalanches. The AERO-FLOW was equipped with a standard drum that was rotated at a speed of 60 rpm for 600 seconds. In each instance, the sample size is 50 mL (milliliters).

As supplied by the manufacturer, the AERO-FLOW device and system is configured to calculate and determine a mean time to avalanche (avalanche-time). The avalanche time provides a flowability index of the sample's flow property. The smaller the avalanche-time, the more flowable the sample. The substantially free-flowing particulate material has a selected avalanche-time.

Gap-Protrusion Area Test Method:

This method allows the testing and screening of materials to determine whether the materials provide desired parameters. Further, it allows a testing of materials to measure the performance of the materials in a manner that is independent of variables introduced by other components. Such other components can, for example, include lofty cover fabrics which may be placed on the body side surface of the structure. This method provides a uniform test sample, applies a defined load-force to the sample by employing the test apparatus, measures a corresponding deformation of the sample that is produced with the test apparatus, and quantifies the deformation of the sample by employing an image analysis system. The applied load-force causes a portion of the sample to move into a channel region, and a cross-sectional area of the material that has moved into this portion is measured. The determination of the Gap-Protrusion Area can employ the following test equipment and procedure.

Gap-Protrusion Area Test Apparatus

The test apparatus employs a loading-force apparatus and scanning apparatus. The loading-force apparatus applies a "standardized" load that simulates a force-condition experienced by the materials during ordinary use. The loading apparatus is constructed to have sufficient strength and rigidity to operatively hold the test sample during the deformation of the sample, and has radiolucent properties that allow for adequate x-ray imaging of the test sample so that the cross-sectional area of the sample can be accurately quantified by the scanning apparatus. Accordingly, the loading-force apparatus was constructed from a combination of high rigidity materials that are operatively radiolucent.

With reference to FIG. 14, a test stand 60 of the loading-force apparatus, includes weights 62, a ram 63, a ram support 64, a leveling base 65, a support base 66, and a sample holder 67. The representatively shown, two weights 62 can be made of any operative material. For example, the weights can be machined from round brass rod, CA Alloy 360. The combined weight of the weights 62 and the ram 63 were arranged to produce a substantially, evenly distributed pressure of 2.5 pound per square inch (17.24 KPa) on an undeformed sample placed beneath it. The base 66 can be constructed of any operative material. For example, the base can be constructed of 0.5 inch (1.27 cm) thick polycarbonate with dimensions of 13 inch×13 inch (33 cm×33 cm). A 5 inch (12.7 cm) diameter hole was drilled through its center.

With reference to FIGS. 15 though 15B, the ram 63 was generally T-shaped with a ram central axis 68, and was configured to allow the weights to be placed onto weight locations 70 that are substantially outside the x-ray beam. The weight locations are symmetrically placed about the ram central axis 68. The top portion 72 of the ram can be made of any operative material. For example, the ram can be machined from light density, KLEGECELL PVC (polyvinyl chloride) foam available from McMaster-Carr, a business having offices located in Chicago, Ill., U.S.A. The dimensions of the top portion of the ram measured 3.5 inch×10 inch (8.9 cm×25.4 cm) with a thickness of 1.5 inch (3.8 cm). The bottom portion 74 can be made of any operative material. For example, the bottom portion can be machined from Owens-Corning FOAMULAR extruded polystyrene insulation board, which is typically employed for building insulation and is readily available from building supply vendors. The dimensions of the bottom portion of the ram measured 1.45 inch×1 inch (3.68 cm×2.54 cm) with a height of 3.38 inch (8.6 cm). The top and bottom portions 72, 74 are operatively attached together. For example, the top and bottom portion can be bonded together with STIX-ALL adhesive from Elmer's Products Inc. The bottom portion 74 also had a 0.25 inch (0.64 cm) wide, rectangular channel-gap or groove 76 machined to a depth of 0.56 inch (1.42 cm) into its bottom surface 78. The groove 76 and the bottom surface 78 of the bottom portion 74 were operatively sealed to substantially prevent a penetration or other capture of particulate material in the foam material, and to provide a smooth low-friction surface for contacting the particles of the test sample. For example, the groove and bottom surface can be sealed with 3-M HIGHLAND 3710 tape available from Minnesota Mining and Manufacturing Company.

With reference to FIGS. 16-16B, the ram support 80 was constructed with a base 84 and a guiding mechanism. For example, the guide device can include the representatively shown, six gussets 82. The ram support can be made of any operative, radiolucent material. For example, the ram support can be constructed from 0.6 inch (1.52 cm) thick, Owens-Corning FOAMULAR extruded polystyrene insulation board. The base 84 had outside dimensions of 9 inch×9 inch (22.9 cm×22.9 cm), and the center of the base 84 was machined with a rectangular hole 86 to operatively receive and pass the ram therethrough. The hole 86 had dimensions of 1.1 inch×1.6 inch (2.79 cm×4.06 cm). An array of generally triangular, guide gussets 82 were arranged on the base 84, as illustrated, and each had overall dimensions of approximately 2 inch by 1.45 inch (5.08 cm×3.68 cm). The two-gusset sets on opposed sides of the rectangular hole 86 were spaced a minimum of 0.5 inch (1.27 cm) apart such that the x-ray beam 98 would pass between them. Ends of the gussets protruded slightly beyond the edges of the hole 86, and were configured to allow a 0.015 inch (0.038 cm) clearance between the gusset ends and the ram 63.

With reference to FIGS. 17-17B, the leveling base 65 can be constructed of any operative material, such as the illustrated two layers of low density KLEGECELL PVC foam available from McMaster-Carr, a business having offices located in Chicago, Ill., U.S.A. The lower layer 88 was machined to the dimensions of 12 inch by 12 inch (30.5 cm by 30.5 cm) with a thickness of 1.5 inch (3.8 cm). This lower layer 88 also contained four conventional leveling screws 90 that were operatively placed at the corners of the lower layer. The top layer 92 had outside dimension of 9 inch by 9 inch (22.9 cm by 22.9 cm) with a thickness of 1.5 inch (3.8 cm), and included a pocket 94 formed therein to receive the sample container 67 (e.g. FIGS. 18-18B). The pocket had dimensions of 4.06 inch by 6.38 inch (10.3 cm×16.2 cm) and a thickness of 1.5 inch (3.8 cm). The two layers of the leveling base 65 were operatively secured together. For example, the layer can be bonded together with STIX-ALL adhesive from Elmer's Products Inc.

With reference to FIGS. 18-18B, the sample holder 67 can be made from any operative material, and can, for example be machined from light density KLEGECELL PVC foam available from McMaster-Carr. The sample holder has outside dimensions of 4 inch by 6.38 inch (10.2 cm×16.2 cm), has a thickness of 1.44 inch (3.66 cm), and includes a pocket or cavity 96 formed therein. The cavity measures 2.75 inch by 2.38 inch (6.98 cm×6.05 cm) with a depth of 0.63 inch (1.6 cm). The corners of the pocket cavity 96 within the sample holder 67 had an inside radius of 0.5 inch (1.27 cm). The cavity 96 was placed within the sample holder 67 such that the ram central axis 68 was aligned with the center of the cavity 96.

With reference to FIG. 19, the scanning apparatus can be provided by a CT (Computed Tomography) scanner system 100. This commercially available, radiological system can be used to collect cross-sectional images of conformable product. Alternatively, other substantially equivalent radiological systems may be employed. For example, other radiological devices can include radiographic devices (e.g., x-ray machines for taking still-images), and fluoroscopic devices (e.g., x-ray machines for that enable an object to be observed directly). Further, systems having other components, such as image recognition equipment for extracting data from conventional x-ray images (i.e., those obtained from radiographic devices or fluoroscopic devices), may also be employed. In the representatively shown configuration, the CT scanner system 100 can include a CT scanner (generally designated by reference numeral 106), an article support (generally designated by reference numeral 102) and a computer console (generally designated by reference numeral 108) for controlling the operation of the CT system. For example, the CT scanner system can include an ANALOGIC ANASCAN Scanner available from Analogic Corporation, a business having offices located in Peabody, Mass., U.S.A.

The CT scanner 106 can include a gantry 110 having an opening 112 for receiving a conformability test apparatus 60 (e.g. FIG. 14). The computer console 108 is operatively connected to the CT scanner 106 for collecting, reconstructing and preparing data for display on an image display monitor 114. The computer console 108 may include one or more input devices such as a keyboard 116.

With reference to FIG. 19A, the tester support 102 for holding the sample and conformance test apparatus 60 has a vertical post 118 mounted on a base 120 having wheels. An arm 122 extends horizontally from the vertical post 118, and a platform 124, is mounted at an end of the arm 122 opposite the post 118. During testing, the conformance test apparatus 60 (e.g. FIG. 14) is placed onto the platform 124. The arm 122 is movable up and down on the post 118 for adjusting a height of the conformability tester 60 relative to the opening 112 in the gantry 110. The wheels on the base 120 of the support 102 permit a horizontal positioning of the test apparatus 60 relative to the opening 112 in the gantry 110. It is further envisioned that the arm 122 may be pivotable with respect to the post 118 to change the orientation of the conformance tester 60 in the gantry 110. The platform 124 comprises a low density frame 126 having a central opening, and grid 128 of low density filaments which extend over the central opening. In one embodiment, the frame 126 can be a rectangular sheet of LEXAN material available from General Electric Company of Pittsfield, Mass. Since the height of the arm 122 can be changed, the sample within the conformability tester 60 can be generally centered in the opening 112 in the gantry 110.

Gap-Protrusion Area Test Procedure

A preconditioned sample is placed in the sample holder 67. For this work, the samples were preconditioned at room temperature and 30-50% relative humidity to minimize static interactions and avoid excessive hydration of the samples. A sample can be either formed in the sample holder, or cut from a larger sample and gently placed in the sample holder. In both cases, the material must fill the entire container of the sample holder with the top surface of the sample material being level with the top surface of the sample holder. Samples of particulate material were made by slowly pouring the particulate material into the sample holder in a manner that creates a substantially uniform, random packing of the particulates which is substantially free of large voids within the sample. For this work, the pouring of the particulate material was conducted over a period of 15 to 30 seconds. After the particulates were placed in the sample holder, excess particulates were removed such that the sample material was level with the top surface of the sample holder, and the top surface of the sample material was substantially uniformly and substantially randomly packed. For this work, a metal, straight-edge ruler was carefully and slowly passed over the sample material to gently scarf off the excess particulates.

The CT scanner system 100 was prepared for operation by energizing the gantry 110 and computer console 108. The computer console 108 is booted, and the user may log in by entering a username and password. The user can then initiate a standard start-up procedure. For the ANALOGIC CT scanner, the computer console 108 offers a "scanner menu". The user selects "warm-up" and then "ok". The user then presses a "start" key on the keyboard 116 when prompted. The user next selects "air tables" under the scanner menu and then "all". The user again presses the "start" key on the keyboard 116 when prompted. After the computer console completes the air tables, the user selects "cancel". Under the "patient menu", the user selects "enter". A warning message concerning warm-up will appear on the monitor 114, and the user selects "cancel". After the start-up, the user may enter information concerning the particular test by entering information in the "patient" menu.

After the sample has been transferred and positioned into the sample holder 67, the sample holder containing the sample material was carefully inserted into the testing stand 60 that was positioned on the article support 102. The conformability tester is positioned on the platform 124 of the support 102, and the gantry 110 is moved to an initial position (e.g., a "350 mm" position) by using controls 130 on the gantry. The position of the article support 102 was determined by passing the scanning system's laser positioning light through the gap between the gussets on the conformability tester 60 where the scanning was to begin. After an appropriate warm-up of the scanner system, the user selects "to scan". The user presses a "scanogram" button on the gantry 110 until the gantry stops moving (e.g., a "67 mm" position). The scanning protocol is selected by selecting "axial" scan type from the menu and then "to scan". In the "scan from" menu, "current position" is selected. Desired information can be input at the prompt. The user selects "gantry" when prompted for a "move unit" and "in" when prompted for a "direction". The desired scanning parameters are selected by selecting "params" and then "ok" when done. A beam thickness, a slice index, a field of view (FOV), an x-axis and a y-axis are set, and "to scan" is selected from the menu. The user reviews the scanning protocol in the "axial scan status" window for correct set-up, de-selects the "corrected" option, enters any desired comments, and selects "scan". For this work a beam thickness of 2 mm, and a field of view of 125 mm was employed with the x-axis and y-axis set to 125 mm and 2 mm, respectively. For this work, the tube settings were 120 kV and 20 mA. The desired algorithm is selected. The "patient position" is set to "headfirst/supine". After reviewing the set up parameters on the monitor 114, the user enters any desired comments and selects "scan". After the area surrounding the gantry 110 is cleared of bystanders, the "start" button is pressed on the keyboard 116 when prompted. A cross-section axial scan image will be shown on the monitor 114. During the sample loading process, the entire testing apparatus was adjusted to ensure that the sample remained level during the process.

When an adequate imaging scan was obtained, the gantry 110 is moved to an initial position (e.g., a "350 mm" position) by using controls 130 on the gantry. The ram 63 was carefully inserted into the ram support 64 until the ram rested on top of the sample. The weights 62 were placed slowly and simultaneously onto the ram. This process of applying the load-force to the sample is conducted in a manner that approximates the application of an ordinary static load. The article support 102 position was determined by passing the scanning system's laser positioning light through the gap between the gussets on the conformability tester 60 where scanning will begin. The user presses a "scanogram" button on the gantry 110 until the gantry stops moving (e.g., a "67 mm" position). The scanning protocol is selected by selecting "axial" scan type from the menu and then "to scan". In the "scan from" menu, "current position" is selected. Desired information can be input at the prompt. The desired scanning parameters are selected by selecting "params" and then "ok" when done. A beam thickness, a slice index, a field of view (FOV), an x-axis and a y-axis are set, and "to scan" is selected from the menu. The user reviews the scanning protocol in the "axial scan status" window for correct set-up, de-selects the "corrected" option, enters any desired comments, and selects "scan". A beam thickness of 2 mm, and a field of view of 125 mm were employed with the x-axis and y-axis set to 125 mm and 2 mm, respectively. Additionally, the tube settings were 120 kV and 20 mA. The desired algorithm is selected. The "patient position" is set to "headfirst/supine". After reviewing the set up parameters on the monitor 114, the user enters any desired comments and selects "scan". After the area surrounding the gantry 110 is cleared of bystanders, the "start" button is pressed on the keyboard 116 when prompted. A cross-section axial scan image will be shown on the monitor 114. When an adequate imaging scan was obtained, the gantry 110 is moved to an initial position (e.g., a "350 mm" position) by using controls 130 on the gantry. The weights 62 were removed slowly and simultaneously from the ram. The ram 63 was carefully removed from support 64 so the sample was completely free of load-force. This process of removing the load-force from the sample is conducted in a manner that approximates the sample conformity after application of an ordinary static load. The article support 102 position was determined by passing the scanning system's laser positioning light through the gap between the gussets on the conformability tester 60 where scanning will begin. The user presses a "scanogram" button on the gantry 110 until the gantry stops moving (e.g., a "67 mm" position). The scanning protocol is selected by selecting "axial" scan type from the menu and then "to scan". In the "scan from" menu, "current position" is selected. Desired information can be input at the prompt. The desired scanning parameters are selected by selecting "params" and then "ok" when done. A beam thickness, a slice index, a field of view (FOV), an x-axis and a y-axis are set, and "to scan" is selected from the menu. The user reviews the scanning protocol in the "axial scan status" window for correct set-up, de-selects the "corrected" option, enters any desired comments, and selects "scan". For this work a beam thickness of 2 mm, and a field of view of 125 mm was employed with the x-axis and y-axis set to 125 mm and 2 mm, respectively. For this work, the tube settings were 120 kV and 20 mA. The desired algorithm is selected. The "patient position" is set to "headfirst/supine". After reviewing the set up parameters on the monitor 114, the user enters any desired comments and selects "scan". After the area surrounding the gantry 110 is cleared of bystanders, the "start" button is pressed on the keyboard 116 when prompted. A cross-section axial scan image will be shown on the monitor 114. When an adequate imaging scan was obtained, the conformability tester 60 was removed from the support platform 124. Once the desired images were acquired, as described above, the images were printed using conventional techniques for the CT scanner system 100. Further, the images were archived to a data storage disk (e.g., an optical disk) using conventional techniques for the particular scanner system. After all the images are printed and archived, the user may exit from the scanner software. For example, the images can be printed six to a page on portrait paper orientation using a commercially available CODONICS printer.

Gap-Protrusion Area Measurements and Calculations

During the gap-protrusion test procedure, a cross-sectional image of the channel region 76 of the ram 63 was obtained, as illustrated in FIG. 20. Each image was analyzed to determine the gap-protrusion value of its corresponding sample. The gap-protrusion value for a selected, example-material was the average of the values obtained from three test samples of the material. Each sample-value was obtained (1) by converting its corresponding optical image into digital image, (2) by identifying the region of the image that corresponded to the sample material that had entered the channel 76, and (3) determining the cross-sectional area of the sample material that had entered the channel 76. The identification of the sample material located in the channel region was determined by observing a difference in the gray scale between the sample material and the material of the ram 63, and by drawing a line across the bottom of the ram 63 to delineate between the sample material that was inside the channel from the sample material that was outside the channel. In particular, the QUANTIMET 970 image analysis system equipment with a CHALNICON scanner, a DCI AUTO-MAC-ROSTAGE, a 50 mm EL-NIKKOR lens (f/2.8) with no extension tubes, and four flood lamps for incident light was employed to convert the optical images to digitized electronic images. The gap-protrusion area was determined with the assistance of a user-defined subroutine. The results from 3 samples for each example material were then averaged to determine the gap-protrusion value for the example material.

Equipment

Conformance testing apparatus, test stand (60), such as disclosed herein.

CT Scanner.

Rigid, straight-edged metal ruler.

Graduated cylinder.

100 ml beaker.

Funnel which fits into graduated cylinder.

Timer.

Spirit level.

Procedure

1. Weigh empty sample holder tray (67). Record weight as A.

2. Prepare materials to be tested as follows:

2.1. Non-Particulate Materials 2.1.1. Cut sample to dimensions that fit easily into the tray.

2.1.2. Gently place the composite into the bottom of the tray.

2.2. Particulates
   2.2.1. Using graduated beaker, scoop approximately 100 mL of material. Slowly pour the particulate material into the sample holder tray over a period of 15 to 30 seconds to provide an excess of particles in the tray.
   2.2.2. With metal straightedge, remove excess material to ensure level testing surface. Remove excess particulates such that the sample material was level with the top surface of the sample holder tray.
3. Re-weigh tray and contents. Record weight as B.
4. Calculate weight of contents as follows:
4.1 Weight of tray and contents (B) minus Empty tray weight (A)=weight of contents.
5. Place conformance test stand on CT scanner table and level using spirit level.
6. Gently place tray and sample contents into conformance test stand and center guide over tray.
7. Scan sample.
8. Gently insert ram into guide and add weights.
9. Ensure test stand is level using spirit level.
10. Position into scanner the sample and test stand, with ram and weights.
11. Scan sample with the ram.
12. Gently remove ram and weights.
13. Scan sample with the ram removed.

To quantify the Gap-protrusion Area shown in the CT scans, the CT scan images were subjected to the following Image Analysis Technique.

Image Analysis Technique for Determining Conformance, Gap-Protrusion Area:

The images obtained from the CT scanner were analyzed through image analysis software. In general terms, the groove or channel-gap region (76) formed in the ram (63) was manually identified and isolated in the scanned image, then the image analysis system was used to determine the area of the sample material that had protruded into the channel-gap under the pressure of the applied load. For example, an "EDITOR" function in the image analysis system may be employed to manually isolate the channel-gap region (76).

With reference to FIG. 20, the schematic CT image representatively illustrates an area 104 of particulate material 28 that has protruded into the channel-gap region of the testing apparatus. The gap-protrusion area 104 is the observed area of the scanned image which corresponds to the portion of the particulate material 28 that has been moved into the channel-gap region 76 of the ram 63 due to the application of the selected 2.5 psi (17.24 KPa) pressure (e.g. generated by the placement of the weights 62 onto the ram 63). As representatively shown, the gap-protrusion area extends from the edge that corresponds to the outside, bottom surface of the ram 63, and projects into the void space provided by the gap region 76. More particularly, CT-scan photographic images (e.g. 6 photos per 8½ inch×11 inch sheet) were placed under glass on a DCI AUTO-MACROSTAGE. Individual photos were scanned with a CHALNICON scanner into a QUANTIMET 970 Image Analysis System using a 50 mm EL-NIKKOR lens, f/2.8, with no extension tubes. Incident light was provided by four flood lamps.

The employed automated routine was as follows:

Enter specimen identify
Scanner (No. 2 Chalnicon LV=0.00 SENS= 1.46 PAUSE)
SUBRTN STANDARD
Load Shading Corrector (pattern-STD)
Calibrate User Specified (Cal Value = 0.09940 millimeters per pixel)
For FIELD
Detect 2D (Lighter than 25, Delin PAUSE)
Amend (CLOSE by 3)
Edit (pause) EDIT
Amend (OPEN by 2)
Measure feature   AREA   PERIMETER   FERET 90   X.FCP
                  Y.FCP
   Into array FEATURE (of 200 features and 7 parameters)
Distribution of COUNT v AREA (Units SQ MM)
   From FEATURE in HISTO1 from 0. to 1000.
   in 1 bins (LIN)
Pause Message
PLEASE CHOOSE ANOTHER GAP
Pause
Next FIELD
Print " "
Print Distribution ( HISTO1, differential, bar chart, scale = 0.00)
For LOOPCOUNT = 1 to 5
Print " "
Next
END OF PROGRAM The following Examples describe various configurations of the invention, and are presented to provide a more detailed understanding of the invention. Other arrangements within the scope of the claims will be apparent to one skilled in the art from consideration of the present disclosure.

Examples 1 Through 9

The Gap-Protrusion Area and the Avalanche Time for Samples 1 through 9 are set forth in the following Table 1.

TABLE 1

| Example | Material | Description | Gap-protrusion Area (mm$^2$) | Average time between avalanches, (sec) |
|---|---|---|---|---|
| 1 | ZEOFREE 5175B, as received from vendor | Granulated precipitated silica, available from J. M. Huber, Havre De Grace, Maryland, U.S.A. | 10.4 | 1.81 |
| 2 | ZEOFREE 5175B, particle size distribution optimized for fast flow | As received material, sieved into narrow particle size ranges, then recombined. | 8.5 | Not available |

TABLE 1-continued

| Example | Material | Description | Gap-protrusion Area (mm$^2$) | Average time between avalanches, (sec) |
|---|---|---|---|---|
| 3 | Eucalyptus nits | Eucalyptus pulp processed as described in U.S. Pat. No. 6,409,883 | 22.9 | 3.12 |
| 4 | CELPHERE | Spherulated alpha cellulose available from FMC Corp, Philadelphia, Pennsylvania, U.S.A. | 53.2 | 1.54 |
| 5 | Woodpulp fluff | Bleached southern softwood fluff, available from Kimberly-Clark | 7.2 | Not applicable |
| 6 | EXCEL 110 | Food grade cellulose fiber available from Functional Foods, Elizabethtown, New Jersey, U.S.A. | 22.3 | 4.24 |
| 7 | FAVOR 880 | Polyacrylate superabsorbent available from Stockhausen, Greensboro, North Carolina, U.S.A.; used as received from the vendor | 15.3 | 3.36 |
| 8 | FAVOR 880 | Polyacrylate superabsorbent coated with EXCEL 110, as described in U.S. Pat. No. 6,376,011 | 29.5 | 2.83 |
| 9 | FAVOR 880 | Polyacrylate superabsorbent swollen with 30 gram/gram of physiological saline | 74.5 | 8.52 |

FIG. 21 shows a representative, graphical plot of the values of avalanche-time and gap-protrusion area that were obtained from the samples of particulate material to determine their conformance capability. In desired configurations, the body conformance system can include particles which have properties that lie in desired regions of the graph. The particulates can have a combination of gap-protrusion area and avalanche-time that lie within the area of the graph and are located below distinctive upper-boundary lines. As representatively shown, the boundary lines are linear. Additionally, the boundary lines have distinctive slope values, and pass through particular intercept-points within the area of the graph. With respect to two chosen points on a desired boundary line, the line slope value can be determined by the formula:

$$\text{Slope} = \frac{\Delta(\text{Average time between Avalanches; sec})}{\Delta(\text{gap-protrusion area; mm}^2)}$$

The three boundary lines shown in FIG. 21 have the parameters set forth in the following Table 2.

TABLE 2

| Boundary Line | Intercept Point (A, B) A = Value of gap-protrusion area (mm$^2$) B = Value of average time between avalanches (sec) | Slope Value (sec/mm$^2$) |
|---|---|---|
| L1 | (1, 1) | 0.114 |
| L2 | (10, 1) | 0.111 |
| L3 | (30, 1) | 0.12 |

In a particular aspect of the invention, the conformance system of the invention can include particulate material which exhibits a distinctive combination of "Gap-protrusion area" and "Average time between avalanches", and such combination falls within the area of the graph of FIG. 21 below the first boundary line L1. Another aspect of the conformance system can include particulate material which has a combination of "Gap-protrusion area" and "Average time between avalanches", wherein the combination lies within the area of the graph of FIG. 21 that lies below the second boundary line L2. In a further aspect, the conformance system can include particulate material which exhibits a combination of "Gap-protrusion area" and "Average time between avalanches", wherein the combination is located within the area of the graph of FIG. 21 that is below the third boundary line L3.

It has been found that various factors can affect the ability of a particulate material to conform to the user's body. One factor is the ability of the material to mold to the shape of the user's body under an applied force. This factor can be represented by the measurement of the gap-protrusion area, which applies a substantially static force to a bed of the material being evaluated. The ability of the material to fill the gap in the test frame is a measure of the ability of the material to mold to a user's body under an applied force. The measure, however, is for a single application of force and, in an ordinary-use situation, the user moves, continually shifting the force being applied to the conformance system. The ability of the material to respond to one or more subsequent applications of force may not be completely measured or represented by the factor of gap-protrusion area.

The average avalanche-time measures the ability of the material under test to re-shape its structure in response to movements of the user's body. A material with a small average time between avalanches can readily flow into a new shape in response to movements by the user, while a material with a high average time between avalanches tends to hold its existing shape even under the relatively small force of gravity. A material that possesses a short time between avalanches has a more liquid-like flow during movement and can conform readily to the user's body.

A desired material can have both the ability to mold to the body under the application of a relatively small force, as well as the ability to readily flow into a new shape in response to movements by the wearer. Experiments have shown that a material can adequately provide a desired level of body conformance when a combination of features are present. In particular, the materials in example 1, example 3, and example 9 appear to perform equivalently. The material in example 8 can perform better than the materials in examples 1, 3 and 9; and the material in example 4 can perform better than the materials in example 1, 3, 9 and 8 with regard to shaping itself to the body. In contrast, the materials in examples 6 and 7 did not perform acceptably in tests with users.

A particular aspect of the conformance system of the invention can include a particulate material that has a distinctive combination of the two factors of gap-protrusion area and avalanche-time. While not intending to be bound by any particular theory, one can conclude that when a material has a sufficiently high value of gap-protrusion area (the material responds very readily to an applied force), the conformance system can acceptably perform even though the material exhibits a relatively high value of avalanche-time (relatively poor ability to flow in response to body movement). A newly applied force produced by a change in body position can be sufficient to re-shape the material without the need for a liquid-like flow. The material can readily conform and re-conform in response to the user's body without the wearer perceiving the force required for re-conformance.

Alternatively, when a material has a sufficiently high, liquid-like flow (exhibits a relatively low value of avalanche-time), the material can conform to the user's body with the slightest shift of position by the user, even though the material may not conform well through direct application of force (relatively low value of gap-protrusion area). Additionally, a material can be acceptable while having intermediate values for both avalanche-time and gap-protrusion area (intermediate abilities to conform through direct force and through dynamically induced particle flow). The acceptable combinations of response to force and dynamically-induced flow (gap-protrusion area and average avalanche-time, respectively) can be determined with respect to the boundary line L1 shown in FIG. 21. The combinations of these properties that are in the area of the graph below the values on the line will be acceptable in use. The further one goes below the line, the more successful the material will be in conforming to the body.

The above-disclosed Examples are not intended to limit the scope of the present invention in any way. It is intended that the specification, together with the Examples, be considered exemplary only, with the scope and spirit of the invention being indicated by the claims which follow. Various modifications and other embodiments and uses of the disclosed superabsorbent-containing composites, apparent to those of ordinary skill in the art, are also considered to be within the scope of the present invention.

The invention claimed is:

1. An absorbent article, comprising: an absorbent retention portion; and a body-conformance system which is positioned at least operatively proximate a bodyside surface of said article; said body conformance system including at least one liquid-permeable, flexible containment layer, and an operative quantity of substantially free-flowing particulate material being entirely surrounded and enclosed by said at least one flexible containment layer; said substantially free-flowing particulate material having an avalanche-time of less than 10 sec between avalanches, and a retention capacity that is within the range of about 1-15 g/g menses-simulant; said substantially free-flowing particulate material including an adsorbent material that neither substantially softens nor substantially swells during its handling of liquids; said adsorbent material being selected from the group consisting of activated carbon, silicates, granulated silica, perlite, vermiculate, granulated clay, glass beads, metal oxides, zeolites, carbonate, phosphates, borates, and aerogels; and said adsorbent material present in an amount which is within the range of about 80 to about 100 wt %, based on a total weight of the adsorbent and other material that is entirely surrounded and enclosed by the at least one flexible containment layer.

2. An absorbent article as recited in claim 1, wherein said substantially free-flowing particulate material has a retention capacity that is within the range of about 8-15 g/g menses-simulant.

3. An absorbent article as recited in claim 1, wherein said body-conformance system is configured to provide a gap-protrusion area of at least about 20 mm$^2$.

4. An absorbent article as recited in claim 3, wherein said body conformance system provides a gap-protrusion area of at least about 40 mm$^2$.

5. An absorbent article as recited in claim 1, wherein said containment layer is configured to be physiologically hydrous.

6. An absorbent article as recited in claim 1, wherein said containment layer is configured to provide an intake-handling time of not more than about 120 sec per 2 mL of menses-simulant at a flow rate of 250 mL/hr.

7. An absorbent article as recited in claim 1, further including substantially liquid-impermeable backsheet layer which is operatively joined with said containment layer.

8. An absorbent article as recited in claim 7, further including a liquid-permeable bodyside layer joined to said backsheet layer.

9. An absorbent article as recited in claim 8, wherein said liquid-permeable bodyside layer is configured to be physiologically hydrous.

10. An absorbent article as recited in claim 1, wherein the containment layer and the held particulate material are configured to provide an intake-handling time of not more than about 120 sec per 2 mL of menses-simulant at a flow rate of 250 mL/hr.

11. An absorbent article as recited in claim 1, wherein said adsorbent material is present in an amount which is within the range of about 90 to about 100 wt %, based on a total weight of the adsorbent and other material that is constrained by the at least one flexible containment layer.

12. An absorbent article as recited in claim 1, wherein said substantially free-flowing particulate material further includes an absorbent material.

13. An absorbent article as recited in claim 1, wherein said retention portion is interposed between the flexible, bodyside containment layer and a backsheet layer.

14. An absorbent article as recited in claim 13, wherein said retention portion has a retention capacity that is within the range of about 1-35 g/g menses-simulant.

15. An absorbent article as recited in claim 14, wherein said retention portion includes superabsorbent.

16. An absorbent article as recited in claim 1, wherein said article further includes a resilient, shaping-layer positioned relatively outward from said quantity of substantially free-flowing particulate material.

17. An absorbent article as recited in claim 1, wherein said body conformance system is configured to provide a selected array of containment pockets.

18. An absorbent article as recited in claim 1, wherein said article is a feminine care article.

19. An absorbent article as recited in claim 1, wherein said article is an interlabial pad.

20. An absorbent article as recited in claim 1, wherein said article is a wound dressing.

21. An absorbent article, comprising:
a backsheet layer;
an absorbent retention portion operatively joined to said backsheet layer; and
a body-conformance system which is positioned at least operatively proximate a bodyside surface of said article;
said retention portion having an absorbent retention capacity within the range of about 2-50 g/g saline;
said body conformance system including
at least one flexible, liquid-permeable containment layer, and
an operative quantity of substantially free-flowing particulate material constrained by said at least one flexible containment layer;
said substantially free-flowing particulate material including an adsorbent material that neither substantially softens nor substantially swells during its handling of liquids, said adsorbent material being selected from the group consisting of activated carbon, silicates, granulated silica, perlite, vermiculate, granulated clay, glass beads, metal oxides, zeolites, carbonate, phosphates, borates, and aerogels;
said adsorbent material present in an amount which is within the range of about 80 to about 100 wt %, based on a total weight of the adsorbent and other material that is constrained by the at least one flexible containment layer;
said substantially free-flowing particulate material having an avalanche-time of less than 10 sec between avalanches, and
said body-conformance system providing a gap-protrusion area of at least about 20 mm$^2$.

22. An absorbent article as recited in claim 21, wherein said article is an adult care article.

23. An absorbent article as recited in claim 21, wherein said article is an infant care article.

24. An absorbent article as recited in claim 21, wherein said article is a child care article.

25. An absorbent article, comprising:
an absorbent retention portion, and a body-conformance system which is positioned at least operatively proximate a bodyside surface of said article;
said body conformance system including
at least one liquid-permeable, flexible containment layer, and
an operative quantity of substantially free-flowing particulate material constrained by said at least one flexible containment layer;
said substantially free-flowing particulate material including an adsorbent material that neither substantially softens nor substantially swells during its handling of liquids, said adsorbent material being selected from the group consisting of activated carbon, silicates, granulated silica, perlite, vermiculate, granulated clay, glass beads, metal oxides, zeolites, carbonate, phosphates, borates, and aerogels;
said adsorbent material present in an amount which is within the range of about 80 to about 100 wt %, based on a total weight of the adsorbent and other material that is constrained by the at least one flexible containment layer;
said substantially free-flowing particulate material having a gap-protrusion area of at least about 20 mm$^2$, and
a retention capacity that is within the range of about 1-15 g/g menses-simulant.

* * * * *